United States Patent [19]
Kriesel et al.

[11] Patent Number: 6,159,180
[45] Date of Patent: Dec. 12, 2000

[54] FLUID DELIVERY APPARATUS WITH FLOW INDICATOR AND VIAL FILL

[75] Inventors: Marshall S. Kriesel, St. Paul; Steven M. Arnold, Minnetanka; James Garrison, South Minneapolis; Farhad Kazemzadeh, Bloomington, all of Minn.

[73] Assignee: Science Incorporated, Bloomington, Minn.

[21] Appl. No.: 09/139,605

[22] Filed: Aug. 24, 1998

Related U.S. Application Data

[62] Division of application No. 08/768,663, Dec. 18, 1996, Pat. No. 5,840,071.

[51] Int. Cl.$^7$ .................................................. A61M 37/00
[52] U.S. Cl. ........................ 604/132; 604/153; 604/246; 604/890.1
[58] Field of Search ............................... 604/132, 82, 83, 604/85, 86, 89, 122, 123, 131, 151, 153, 246, 415, 416, 890.1; 128/DIG. 12

[56] References Cited

U.S. PATENT DOCUMENTS

| | | | |
|---|---|---|---|
| 4,968,301 | 11/1990 | Palma et al. | 604/132 |
| 5,176,641 | 1/1993 | Idriss | 604/133 |
| 5,257,987 | 11/1993 | Athayde et al. | 604/892.1 |
| 5,263,935 | 11/1993 | Hessel | 604/132 |

Primary Examiner—Corrine McDermott
Assistant Examiner—Kevin C. Sirmons
Attorney, Agent, or Firm—James E. Brunton

[57] ABSTRACT

An apparatus for accurately infusing medicinal agents into an ambulatory patient at specific rates over extended periods of time. The apparatus is of a compact, low profile, laminate construction and includes an elastic distendable membrane, chamber having a fluid outlet. Disposed within the fluid chamber is a thin fluid permeable member which precisely controls the rate of fluid flow through the fluid outlet. The apparatus also includes a highly novel fluid flow indicator that provides a readily discernible visible indication of fluid flow through the apparatus. Additionally, the apparatus includes a fill assembly comprising a prefilled vial that can be used to fill the fluid reservoir of the device with a selected medicinal fluid.

4 Claims, 21 Drawing Sheets

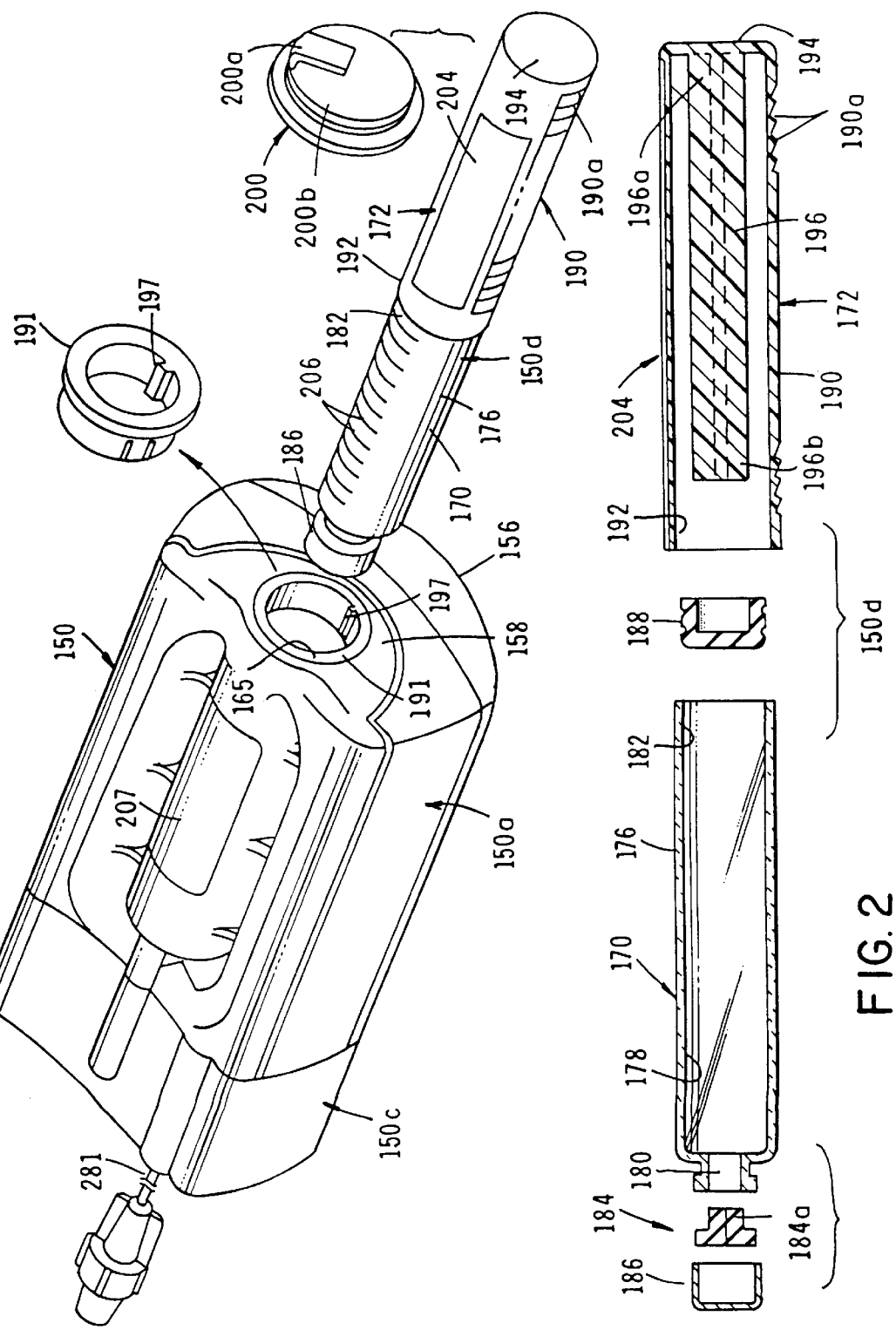

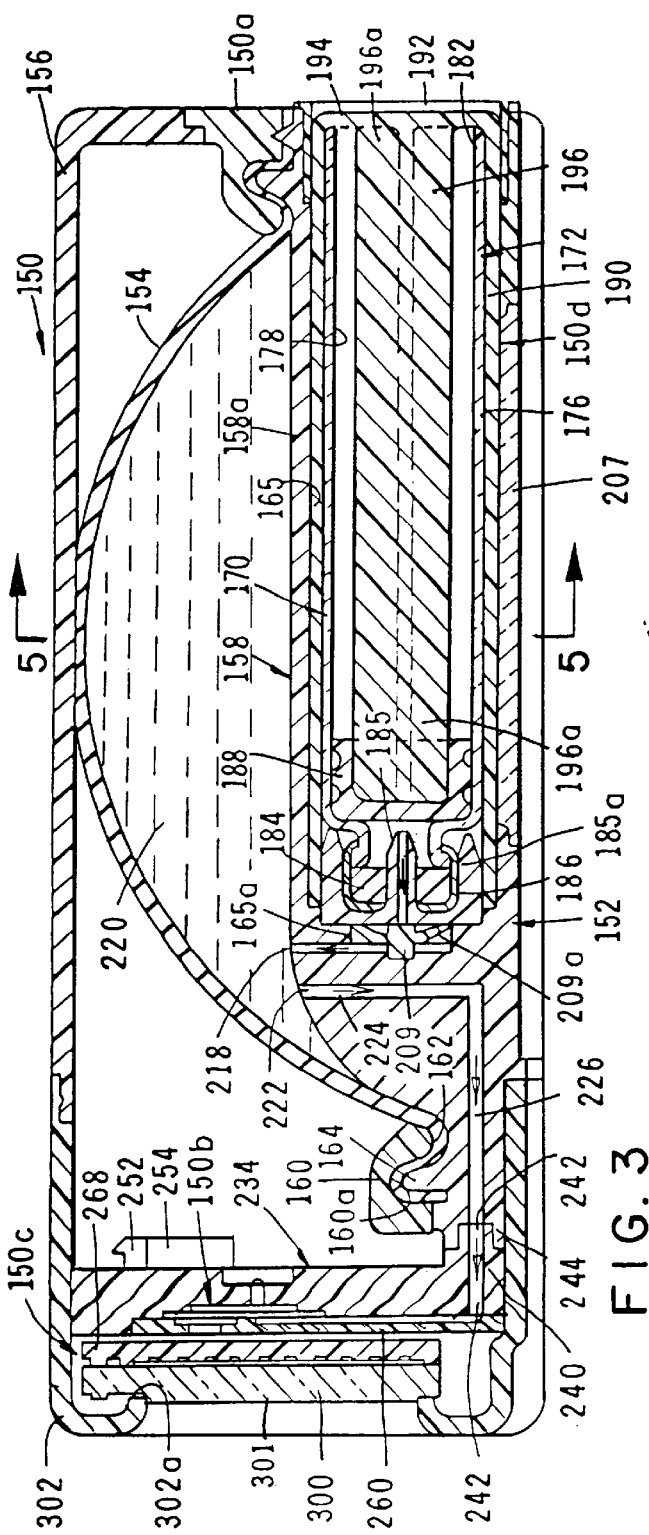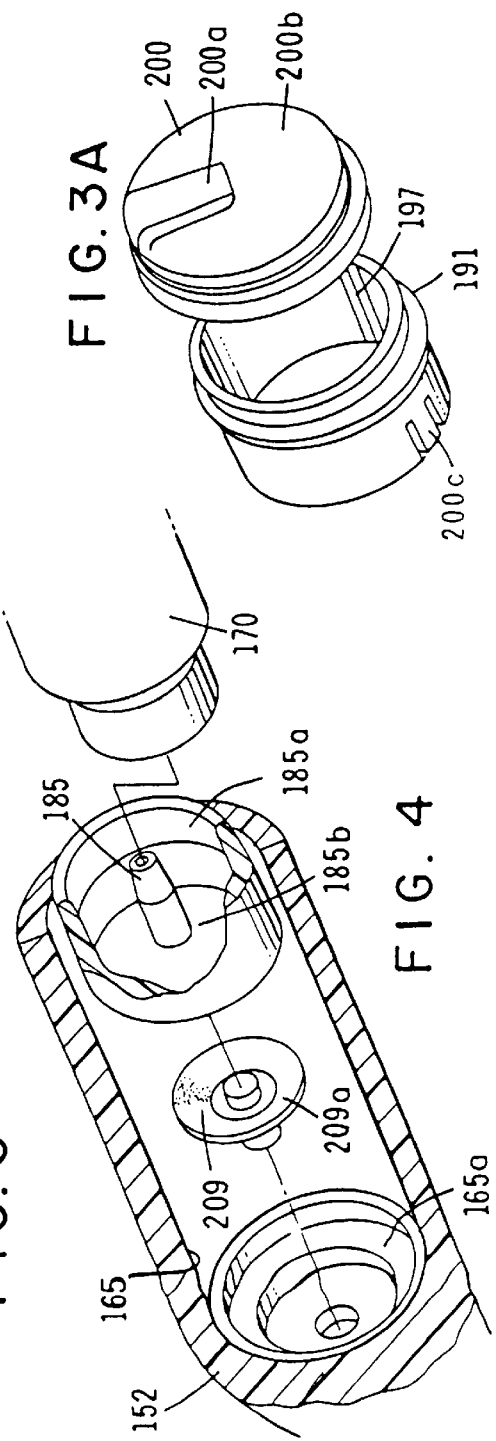

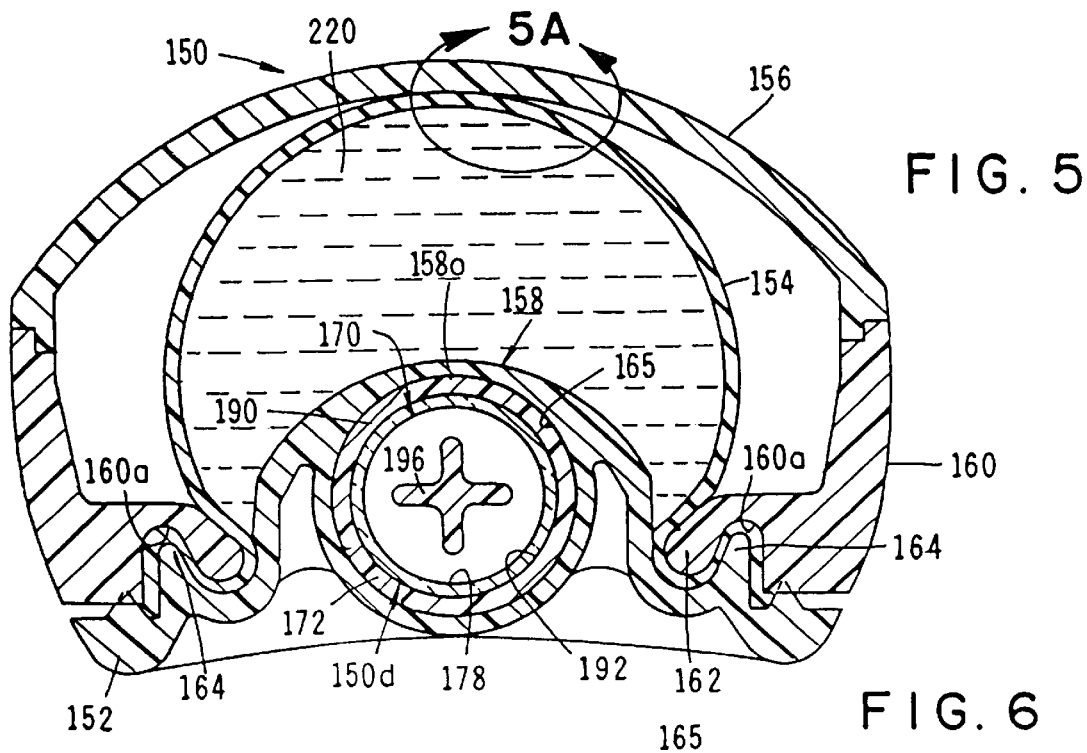
FIG. 5
FIG. 5A
FIG. 6
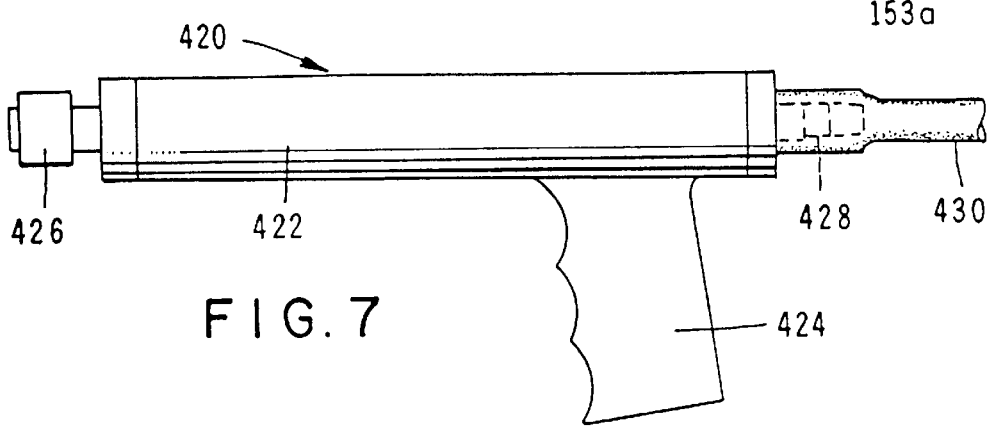
FIG. 7

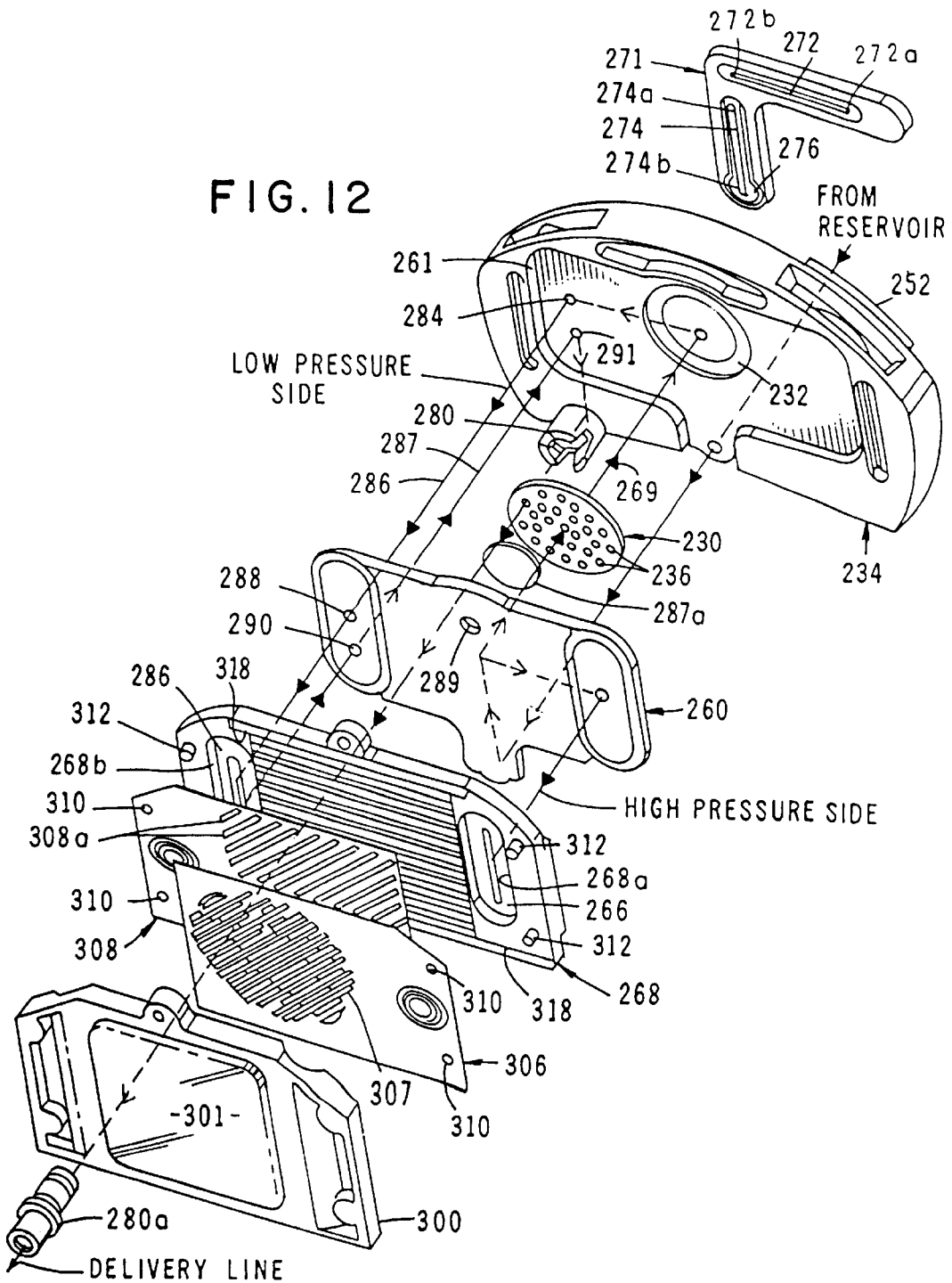

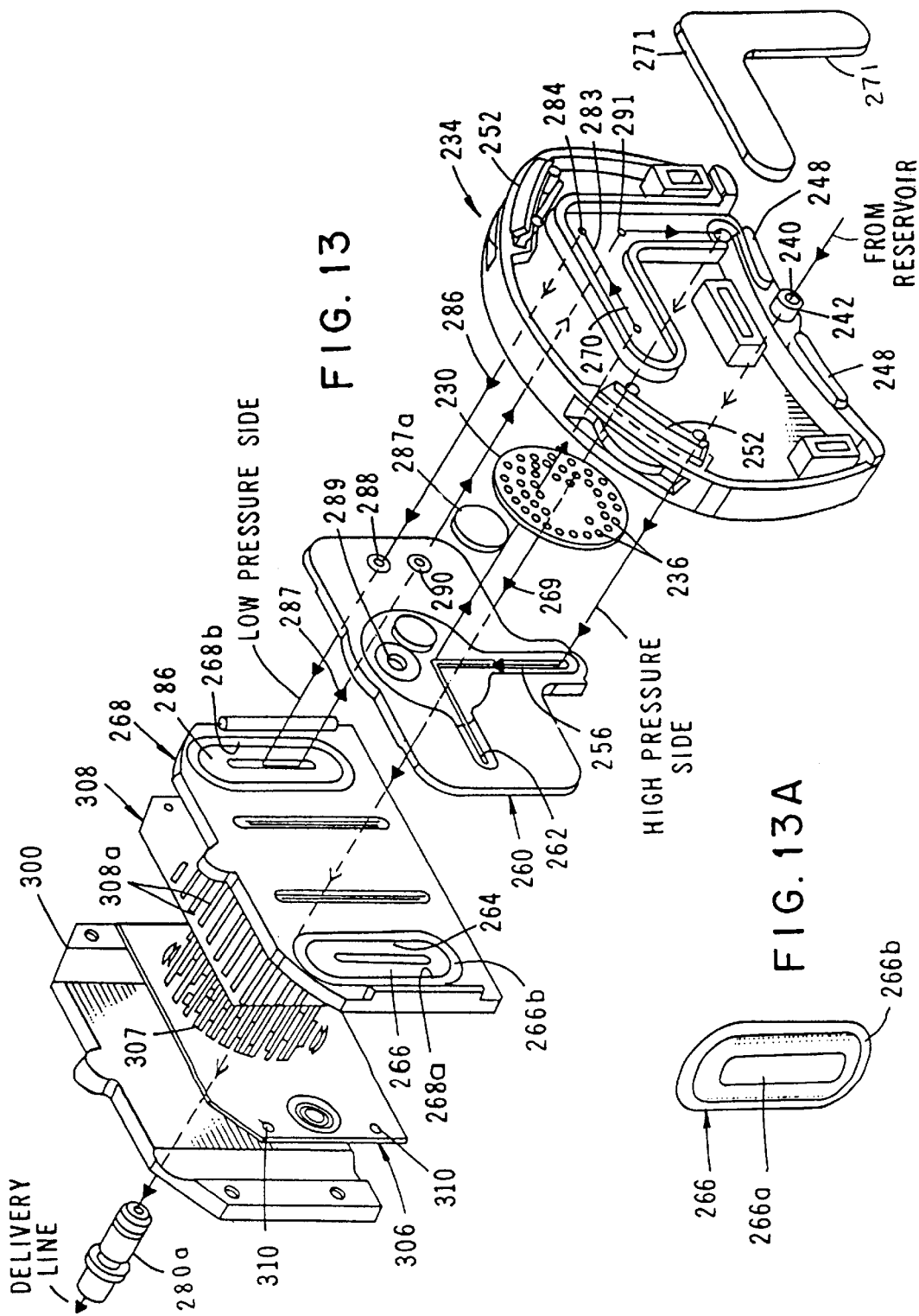

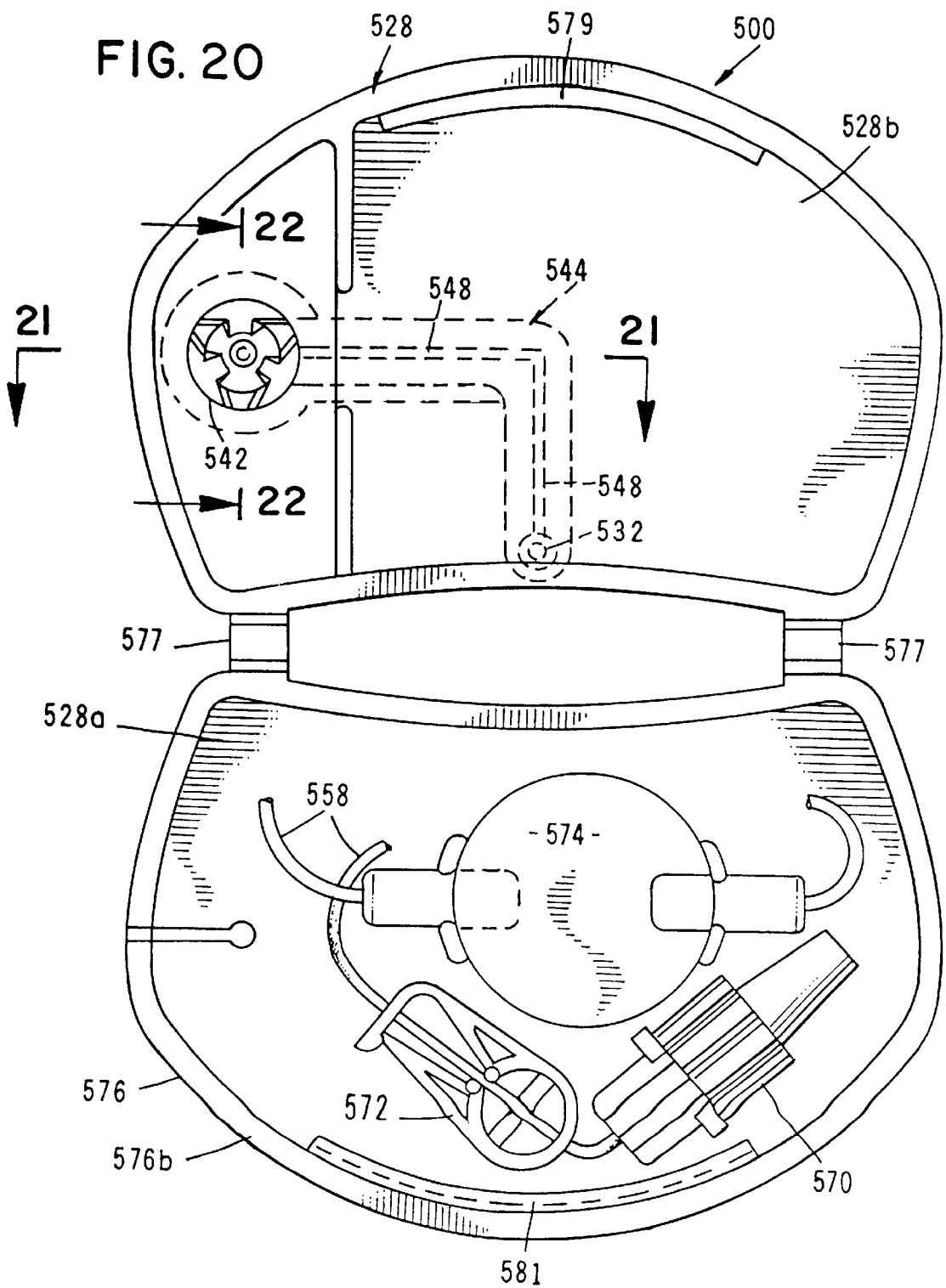

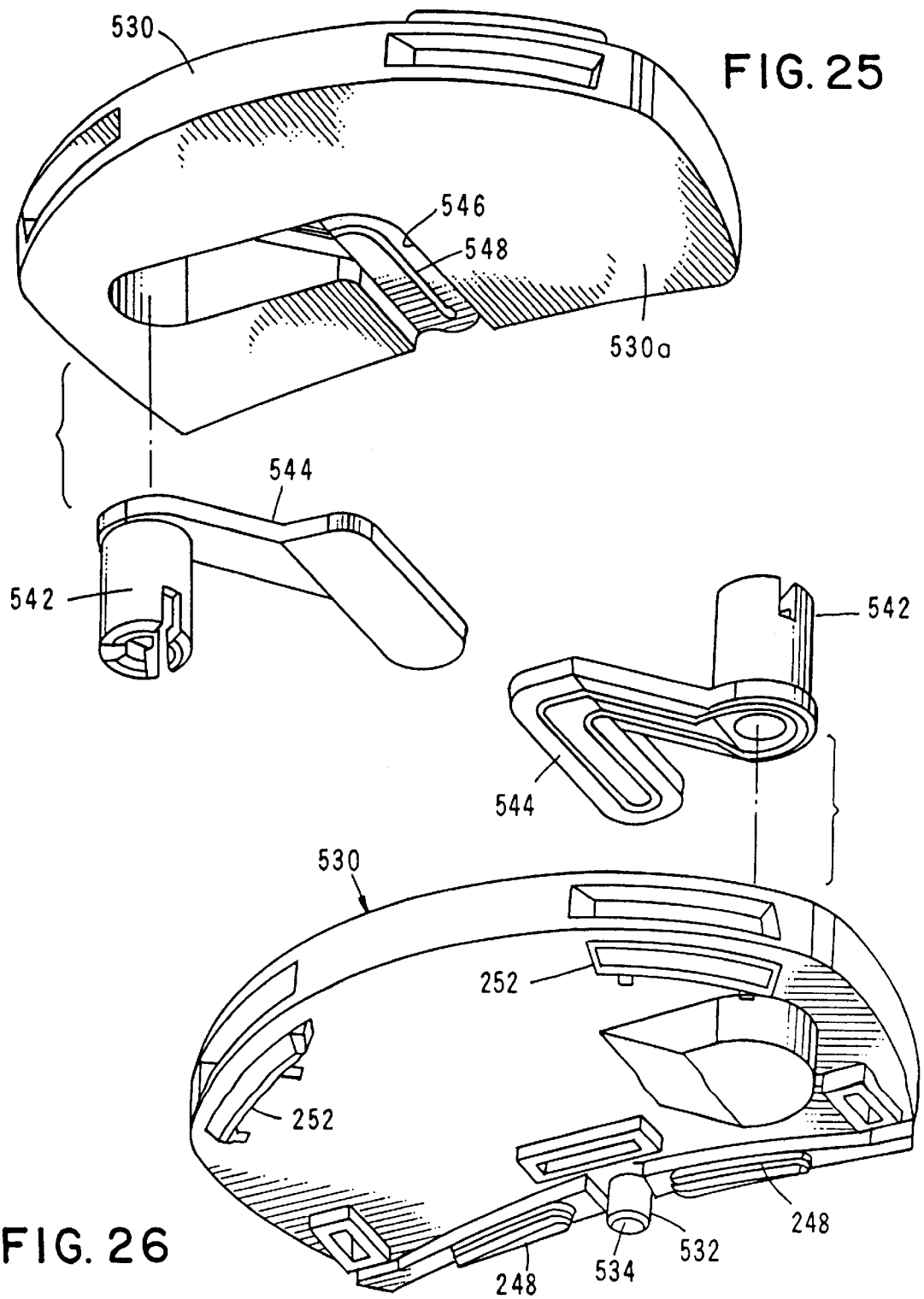

FLUID DELIVERY APPARATUS WITH FLOW INDICATOR AND VIAL FILL

This is a Divisional Application of U.S. application Ser. No. 08/768,663 filed Dec. 18, 1996, now U.S. Pat. No. 5,840,071.

BACKGROUND OF THE INVENTION

1. Field of the Invention

The present invention relates generally to fluid delivery devices. More particularly, the invention concerns an improved apparatus for infusing medicinal agents into an ambulatory patient at specific visual rates over extended periods of time, which apparatus includes both flow indicators means and a novel vial assembly fill means for filling the reservoir of the device.

2. Discussion of the Invention

Many medicinal agents require an intravenous route for administration thus bypassing the digestive system and precluding degradation by the catalytic enzymes in the digestive tract and the liver. The use of more potent medications at elevated concentrations has also increased the need for accuracy in controlling the delivery df such drugs. The delivery device, while not an active pharmacologic agent, may enhance the activity of the drug by mediating its therapeutic effectiveness. Certain classes of new pharmacologic agents possess a very narrow range of therapeutic effectiveness, for instance, too small a dose results in no effect, while too great a dose results in toxic reaction.

In the past, prolonged infusion of fluids has generally been accomplished using gravity flow methods, which typically involve the use of intravenous administration sets and the familiar bottle suspended above the patient. Such methods are cumbersome, imprecise and require bed confinement of the patient. Periodic monitoring of the apparatus by the nurse or doctor is required to detect malfunctions of the infusion apparatus.

Devices from which liquid is expelled from a relatively thick-walled bladder by internal stresses within the distended bladder are well-known in the prior art. Such bladder, or "balloon" type, devices are described in U.S. Pat. No. 3,469,578, issued to Bierman and in U.S. Pat. No. 4,318,400, issued to Perry. The devices of the aforementioned patents also disclose the use of fluid flow restrictors external of the bladder for regulating the rate of fluid flow from the bladder.

The prior art bladder type infusion devices are not without drawbacks. Generally, because of the very nature of the bladder or "balloon" configuration, the devices are unwieldy and are difficult and expensive to manufacture and use. Further, the devices are somewhat unreliable and their fluid discharge rates are frequently imprecise.

The apparatus of the present invention overcomes many of the drawbacks of the prior art by eliminating the bladder and making use of recently developed elastomeric films and similar materials, which, in cooperation with a base define a fluid chamber that contains the fluid which is to be dispensed. The elastomeric film membrane controllably forces fluid within the chamber into fluid flow channels provided in the base.

The elastomeric film materials used in the apparatus of the present invention, as well as various alternate constructions of the apparatus, are described in detail in U.S. Pat. No. 5,205,820 issued to the present inventor. Therefore, U.S. Pat. No. 5,205,820 is hereby incorporated by reference in its entirety as though fully set forth herein. Co-pending U.S. Ser. No. 08/046,438 filed by the present inventor on May 18, 1993 also describes various alternate constructions and modified physical embodiments of the invention. This co-pending application is also hereby incorporated by reference in its entirety as though fully set forth herein. Because the present application discloses a novel improvement to the apparatus described in co-pending U.S. Ser. No. 08/432,221 filed May 1, 1995, this co-pending application is also hereby incorporated by reference in its entirety as though fully set forth herein.

The apparatus of the present invention can be used with minimal professional assistance in an alternate health care environment, such as the home. By way of example, devices of the invention can be comfortably and conveniently removably affixed to the patient's body and can be used for the continuous infusion of antibiotics, hormones, steroids, blood clotting agents, analgesics, and like medicinal agents. Similarly, the devices can be used for I-V chemotherapy and can accurately deliver fluids to the patient in precisely the correct quantities and at extended microfusion rates over time.

The embodiments of the invention described in Ser. No. 08/432,221, which application is incorporated herein by reference, comprises a fluid delivery apparatus having a fluid reservoir, fluid flow control assembly, and an indicator assembly for indicating fluid flow through the apparatus. However, unlike the apparatus of the present invention, which includes a unique vial fill assembly for filling the reservoir, the reservoir of the apparatus described in Ser. No. 08/432,221 is filled from an external fluid source which is connected to a conventional luer connector provided on the base of the device. As will be better understood from the description which follows, the novel vial fill assembly of the present invention significantly expands the capability of the apparatus, including enabling the reservoir of the device to be filled at time of usability to controllably fill the reservoir of the device with a wide variety of medicinal fluids that can be conveniently stored within the prefilled vial component of the vial assembly.

SUMMARY OF THE INVENTION

It is an object of the present invention to provide an apparatus for expelling fluids at a precisely controlled rate which is of a compact, low profile, laminate construction. More particularly, it is an object of the invention to provide such an apparatus which can be used for the precise infusion of pharmaceutical fluids to an ambulatory patient at controlled rates over extended periods of time.

It is another object of the invention to provide an apparatus of the aforementioned character which is highly reliable and easy-to-use by lay persons in a non-hospital environment.

Another object of the invention is to provide an apparatus which can be factory prefilled with a wide variety of medicinal fluids or one which can readily be filled in the field shortly prior to use.

A further object of the invention is to provide a low profile, fluid delivery device of laminate construction which can be manufactured inexpensively in large volume by automated machinery.

Another object of the invention is to provide a device of the aforementioned character which includes a novel rate control membrane disposed intermediate the fluid reservoir outlet and the outlet port of the device.

Another object of the invention is to provide a device of the character described which embodies a highly novel fluid flow indicator that provides a readily discernible visual indication of fluid flow status through the device.

Another object of the invention is to provide an apparatus of the aforementioned character in which the stored energy source is of a novel laminate construction which can be precisely tailored to deliver fluid from the device at precise rates.

Another object of the invention is to provide a unique fill assembly for use in controllably filling the fluid reservoir of the apparatus.

Another object of the present invention is to provide an apparatus of the aforementioned character in which the fill assembly comprises a vial assembly that can be prefilled with a wide variety of medicinal fluids.

Another object of the present invention is to provide a fill assembly of the type described in the preceding paragraph in which the prefilled vial assembly is partially received within the housing of the fluid dispensing device for operable interconnection therewith.

Another object of the invention is to provide an apparatus as described in the preceding paragraphs which includes locking means for locking the vial assembly to the fluid delivery assembly following filling of the fluid reservoir.

Another object of the invention is to provide a novel vial assembly for use with the fluid dispenser subassembly of the apparatus which is easy to use, is inexpensive to manufacture, and one which maintains the vial in an aseptic condition until time of use.

Other objects of the invention are set forth in U.S. Pat. No. 5,205,820 which is incorporated herein and still further objects will become more apparent from the discussion which follows.

By way of summary, the improved fluid delivery apparatus of the present form of the invention comprises four cooperating subassemblies, namely a reservoir assembly, a fluid flow control subassembly, a flow indicator subassembly and a reservoir fill assembly. The reservoir subassembly, which readily lends itself to automated manufacture, is generally similar to that described in copending Ser. No. 08/432,221 and includes a base and a stored energy means comprising at least one distendable elastomeric membrane which cooperates with the base to form a fluid reservoir. The fluid flow control subassembly is also similar to that described in Ser. No. 08/432,221 in that it comprises a thin permeable flow control membrane which controls the rate of flow of fluid flowing toward the outlet port of the device.

As will be discussed in greater detail hereinafter, the highly novel fluid flow indicator means of the invention comprises a mechanical fluid flow indicator that provides a clear visual indication of normal fluid flow and absence of fluid flow either because the reservoir is empty or because the flow lines are occluded. More particularly, symbols indicating the operating condition of the device are produced by the movement of thin, indicia-carrying films. These films, which comprise a part of the flow indicator means, are shifted by the movement of mechanical actuators which are deflected solely by the fluid pressure within the device. The fluid flow indicator design does not invade the fluid flow path and yet utilizes the same stored energy means to generate fluid pressure that provides for the normal functioning of the device. The fluid flow indicator is highly reliable in operation, can be produced inexpensively, and, because it has very few parts, is easy to manufacture.

As previously mentioned, the novel fill assembly for use in filling the reservoir of the reservoir assembly comprises a novel vial assembly which can be operably mated with the reservoir assembly for the controlled filling thereof at time of use.

BRIEF DESCRIPTION OF THE DRAWINGS

FIG. 1 is an exploded, generally perspective bottom view of one form of the apparatus of the present invention in which the reservoir of the fluid delivery device is filled by a vial assembly of novel construction.

FIG. 2 is a side-elevational, cross-sectional, exploded view of the vial assembly shown in FIG. 1.

FIG. 3 is a side-elevational, cross-sectional view of the apparatus of FIG. 1 showing the vial assembly coupled with the reservoir assembly of the fluid delivery device.

FIG. 3A is a generally perspective exploded view of the sterile cover subassembly of the invention for closing the vial assembly receiving chamber of the fluid delivery device.

FIG. 4 is an enlarged, generally perspective, exploded view of the vial assembly receiving chamber of the reservoir assembly showing the vial assembly in position to be mated with the reservoir assembly.

FIG. 5 is a cross-sectional view taken along lines 5—5 of FIG. 3.

FIG. 5A is a fragmentary, cross-sectional view of the area designated as 5A in FIG. 5.

FIG. 6 is a fragmentary, cross-sectional view similar to FIG. 5, but showing an alternate form of membrane capture means.

FIG. 7 is a side-elevational view of an alternate form of reservoir fill assembly.

FIG. 12 is a generally perspective, exploded view of one form of the flow control and flow indicator means of the invention.

FIG. 13 is a generally perspective, exploded view similar to FIG. 12 also illustrating the construction of the alternate form of flow control and indicator means of the invention.

FIG. 13A is a generally perspective view of one form of the elastomeric boot component of the indicator means of the invention which, in response to fluid pressure, acts upon the indicia carrying means of the flow indicating means.

FIG. 20 is a front view of the apparatus showing the closure means of the invention in an open configuration.

FIG. 25 is an exploded, generally perspective front view of the support structure of the fluid delivery apparatus of the form of the invention shown in FIGS. 17 and 18

FIG. 26 is an exploded, generally perspective, rear view of the apparatus shown in FIG. 25.

DESCRIPTION OF THE INVENTION

Figure 8:
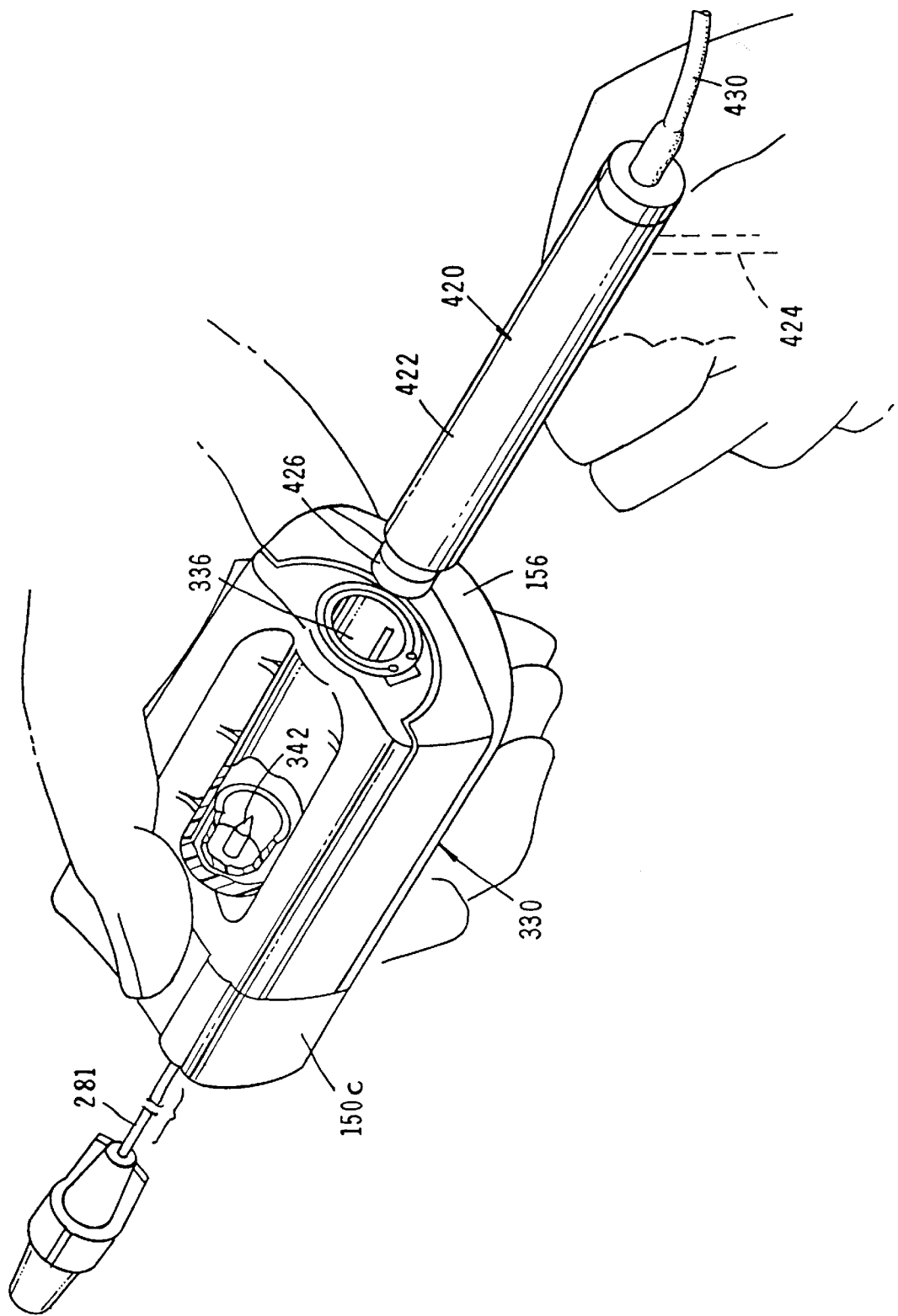
FIG. 8 is a generally perspective bottom view illustrating the manner of filling the reservoir using the reservoir fill assembly shown in FIG. 7.

Referring to the drawings and particularly to FIGS. 1 through 5, the apparatus of this form of the present invention is there illustrated and identified generally by the numeral 150. In order to avoid possible confusion with the numbering of U.S. Ser. No. 08/432,221, which is incorporated herein by reference, numbering of the drawings of the application will start with the numeral 150.

As best seen in FIGS. 1 and 3, the apparatus here comprises four major cooperating subassemblies namely, a reservoir subassembly 150a, a flow rate control subassembly 150b, a flow indicator subassembly 150c and a fill assembly 150d. Each of these subassemblies will be discussed in greater detail in the paragraphs which follow.

Considering first the reservoir subassembly shown in FIG. 3, this subassembly includes a base assembly 152, a stored energy source, shown here as a distendable membrane component 154, and a cover 156 for enclosing the stored energy source. The base assembly includes an ullage substrate 158 and a membrane capture housing 160 having a bottom opening 162 which receives the distendable membrane engaging element or protuberance 164 (see also FIG. 5) of base assembly 152.

Referring particularly to FIGS. 3 and 5, the ullage substrate 158 is provided with fill assembly receiving means shown here as a longitudinally extending, generally cylindrically shaped receiving chamber 165 for receiving the fill assembly 150d. Provided within chamber 165 are the valve and cannula means of the invention, the nature and purpose of which will presently be discussed. As best seen by referring to FIGS. 1 and 2, one form of the fill assembly 150d of the apparatus comprises a container subassembly 170 and an adapter subassembly 172. Container subassembly 170 includes a body portion 176, having a fluid chamber 178 for containing an injectable fluid. Chamber 178 is provided with first and second open ends 180 and 182 (FIG. 2). First open end 180 is sealably closed by closure means here provided in the form of a pierceable septum assembly 184 which includes a septum 184a. Septum 184a is pierceable by the cannula means of the invention which is shown in FIGS. 3 and 4 as a blunt end, hollow cannula 185. Septum assembly 184 is held securely in position within open end 180 by clamping ring 186. As best seen in FIG. 2 and 3, to expel fluid from chamber 178, a plunger 188 is telescopically movable within the chamber from a first location where it is proximate second open end 182 to a second position shown in FIG. 3 where it is proximate first open end 180. The vial or body portion of the container subassembly 170 can be constructed of various materials such as glass and plastic.

Referring particularly to FIG. 2, it can be seen that the adapter subassembly 172 of this form of the invention comprises a hollow housing 190 in the manner shown in having a first open end 192 and a second closed end 194. Container subassembly 170 is telescopically receivable within open end 192 of housing 190 in the manner shown in the drawings so that the housing can be moved from the first extended position shown in FIG. 1 to the vial encapsulation position shown in FIG. 3. Forming an important part of the adapter subassembly is pusher means shown here as an elongated pusher rod 196 which functions to move plunger 188 within fluid chamber 178 from the first position shown in FIG. 1 to the second position shown in FIG. 3. In the form of the invention shown in the drawings, pusher rod 196 has a first end 196a interconnected with closure wall 194 and an opposite end 196b which engages plunger 188 and causes telescopic movement of the plunger within chamber 178 of container subassembly 170 as housing 190 is moved from the extended position shown in FIG. 1 into the vial encapsulating position shown in FIG. 3.

As best seen by referring to FIGS. 1 and 3, receivable within the mouth of chamber 165 of substrate 158 is a retaining ring 191 having an alignment protuberance 197 which engages and centers adapter subassembly 172 within chamber 165. Due to the small surface area presented by protuberance 197, there is little frictional resistance to the sliding movement of the adapter subassembly relative to base assembly 152 as the adapter subassembly is moved from the extended position shown in FIG. 1 into the vial encapsulating position shown in FIG. 3.

Turning particularly to FIGS. 1, 3, and 3a, it is to be noted that prior to the fill assembly being inserted into chamber 165, the chamber is maintained in a sterile condition by a sterile tear-off cover assemble 200 which is bonded or otherwise removably affixed to retaining ring 191. An integral pull tab 200a is provided to permit the tear-off cover 200b to be pulled from retaining ring 191 so as to permit insertion of the fill assembly into chamber 165. Assembly 200 also includes a resilient tab-like element 200c (FIG. 3A) which lockably engages saw tooth-like protuberances 190a formed on adapter subassembly 172 to prevent removal of the adapter subassembly from chamber 165 after it has been fully inserted therewithin. As best seen in FIG. 1, a medicament label 204 circumscribes adapter portion 172 and serves to identify the contents of container subassembly 170 prior to mating the fill assembly with the dispensing device. It is also to be noted that container subassembly 170 is provided with indicator means shown here as a plurality of spaced-apart index lines 206, which, by viewing the container assembly through a window 207 provided in substrate 158 (FIG. 1), permit the user to determine how much fluid remains within the container at any given time.

As plunger 188 is moved forwardly of container 170 by the insertion of the fill assembly into chamber 165, the fluid contained in the container will flow under pressure into passageway 218 via the valve means which is here provided as an umbrella type check valve 209. As best seen in FIG. 4, valve 209, which is of a conventional construction, is received within a cavity 165a formed in the end wall of receiving chamber 165 and is held in position therewithin by a cylindrically shaped housing 185a having an end wall 185b which supports cannula 185 in the manner shown in FIG. 4. Valve 209 is constructed from an appropriate elastomer and has a resiliently deformable skirt portion 209a which will deform inwardly within cavity 165a to permit fluid to flow toward the reservoir of the device, but will block reverse flow. From passageway 218, the fluid will flow under pressure into reservoir 220 where it will cause the stored energy means or membrane 154 to distend outwardly from protuberance 158a of ullage substrate 158 in the manner shown in FIGS. 3 and 5.

As before, the stored energy means can be in the form of a single prestressed or unstressed isotropic, elastomeric distendable membrane, or it can comprise a laminate assemblage made up of a plurality of initially generally planar distendable elements or films. In particular, as shown in FIG. 5A, the layer 154a that will be in contact with the fluid may be a fluoroelastomer coating of the type made by Lauren International, Inc. that is known by the tradename Flurolast WB$^R$. The outer layer 154 can be any suitable elastomer having the characteristics best suited for the end application to be made of the device. As previously discussed, as the distendable membrane 154 is distended by the fluid pressure exerted by the fluid flowing into the reservoir, internal stresses are formed therein which continuously urge the assemblage toward engagement with protuberance 158a as it tends to return toward its original configuration. As the membrane moves toward protuberance 158a, fluid within reservoir 220 will be uniformly and controllably forced outwardly through reservoir outlet 222, through passageway 224 and finally through longitudinally extending passageway 226 which is formed in ullage substrate 158.

As indicated by FIGS. 3 and 5, upstanding tongue 164 of base 152 extends completely about the perimeter of the base and is closely receivable within a groove 160a of capture housing 160. When the ullage substrate and the membrane capture housing are assembled in the manner shown in FIGS. 3 and 5, the periphery of distendable membrane 154 will be securely clamped within groove 160a by tongue 164.

After the parts are thus assembled, housing 160 is bonded to base 152 by any suitable means such as adhesive or sonic bonding. This done, cover 156 is mated with capture housing 160 in the manner shown in FIGS. 3 and 5 and bonded in place.

Referring next to FIG. 6, an alternate form of the apparatus of the invention is there shown. This embodiment is virtually identical in construction and operation to that shown in FIGS. 3 and 5 save that the base 153 is provided with a pair of circumferentially extending tongues 153a which tongues are closely receivable within a pair of grooves 161a provided in the capture housing 161. With this construction, when the modified ullage substrate and the modified membrane capture housing are assembled in the manner shown in FIG. 6, the periphery of distendable membrane 154 will be securely clamped within grooves 161a by tongues 153a. After the parts are thus assembled, housing 161 is bonded to base 153 by any suitable means such as adhesive or sonic bonding.

Once again, reference should be made to U.S. Ser. No. 08/432,221 for the various materials that can be used to construct the base assemblies 152 and 153, the cover 156, and the membrane capture housings 160 and 161 as identified in the preceding paragraphs.

Turning now to a consideration of the important flow rate control subassembly of this latest form of the invention, this subassembly is somewhat similar to that previously described and also includes flow control means which are disposed externally of reservoir 220 for controlling the rate of fluid flow of fluid from the device. This flow control means here comprises a rate control means, here shown as membrane 230 (FIG. 12), which is closely received within a circular recess 232 formed in support means shown here as comprising a support structure 234. Rate control membrane 230 comprises a very thin (approximately 0.018 inch thick), rigid polyester plate having a multiplicity of small laser drilled orifices 236. It is to be understood that rate control membrane 230 can be constructed from materials other than polyester, including those materials identified in U.S. Pat. No. 5,205,820 which patent is incorporated herein by reference.

Figure 13B:
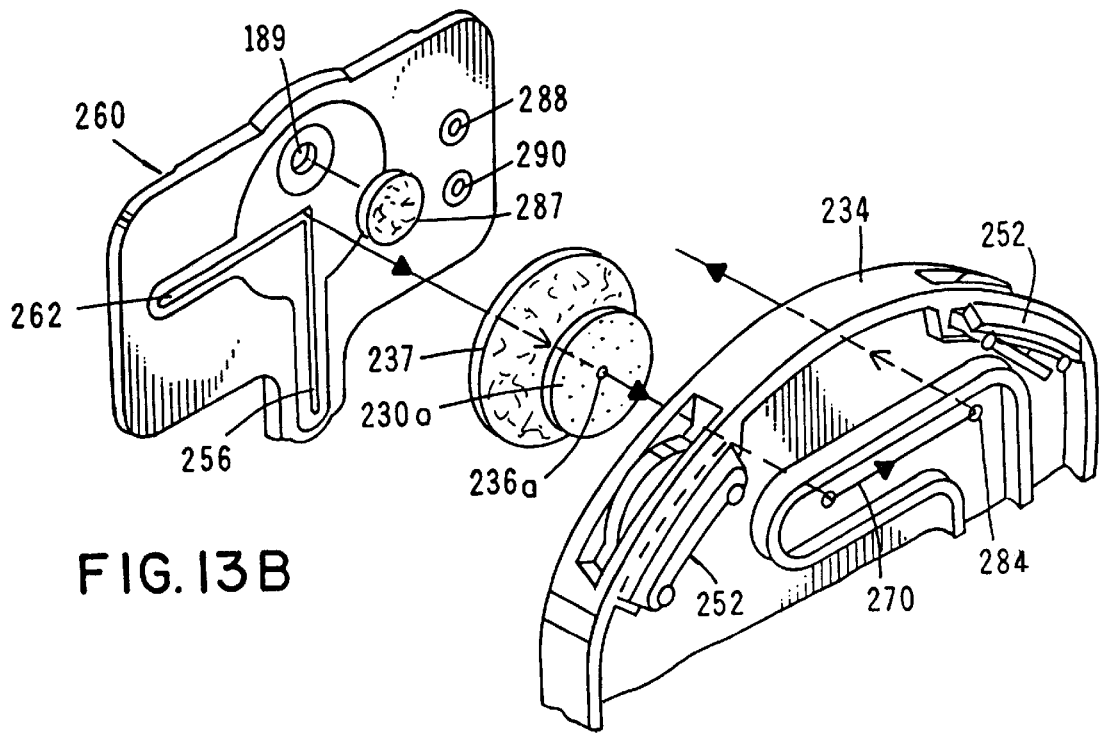
FIG. 13B is a fragmentary, generally perspective view illustrating an alternate form of flow control means of the invention.

Referring to FIG. 13B, an alternate form of the flow control means of the invention is there shown. This flow control means is usable with the various components previously described and here comprises a rate control membrane 230a of slightly different construction, which is closely received within a circular recess 232 formed in support structure 234 (see FIG. 12). Rate control membrane 230a comprises a very thin (approximately 0.018 inch thick), rigid polyester plate having only a single small laser drilled orifice 236a. This rate control membrane 230a can also be constructed from various materials including those materials identified in U.S. Pat. No. 5,205,820.

Also comprising a part of the flow control means of this latest form of the invention is a vent patch or membrane 287, which is of the character previously described, and filter means shown here as a thin membrane 237. Filter membrane 237 is positioned proximate rate control membrane 230a and functions to filter particulates from the fluids flowing from passageway 262 toward rate control membrane 230a (see also FIG. 13). Filter membrane 237 can be constructed from a number of porous materials such as metal and ceramics. A polyether sulfone material sold by Gelman Sciences under the name and style "SUPOR" has also proven satisfactory.

Figure 13C:
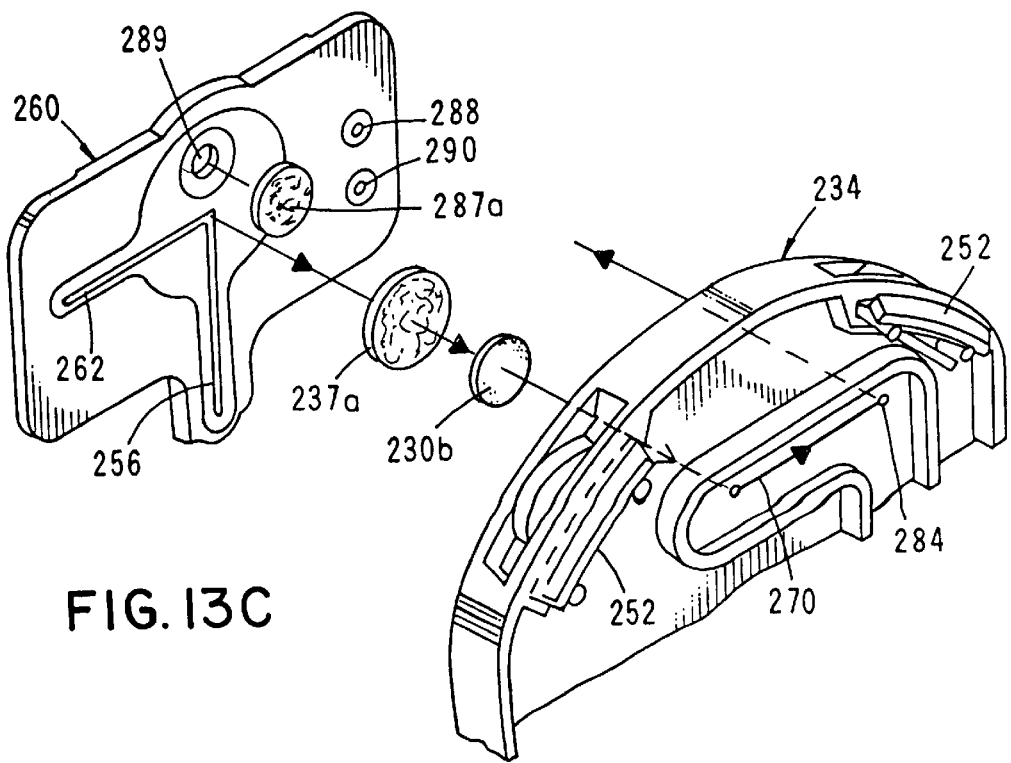
FIG. 13C is a fragmentary, generally perspective view illustrating yet another form of flow control means of the invention.

Turning next to FIG. 13C, still another form of flow control means of the invention is there shown. This flow control means is also usable with various components previously described and here comprises frit or rate control membrane 230b which is also closely received within a circular recess form in support structure 234 (see FIG. 13). Rate control frit 230b here comprises a rigid, porous glass frit of a character well known in the art which can be tailored to provide the desired flow rate.

Also comprising a part of the flow control means of this latest form of the invention is a small version of the previously identified membrane 287, here identified as 287a. Also forming a part of this flow control means is the previously identified filter membrane 237. Filter membrane 237a is positioned proximate rate control frit 230b and, as before, functions to filter particulates from the fluids flowing from passageway 262 toward rate control frit 230b (see FIG. 13).

Support structure 234 includes an outwardly extending generally cylindrically shaped, fluid inlet element 240 (FIG. 13) which is provided is a fluid passageway 242. Passageway 242 is adapted to communicate with reservoir 220 via passageways 224 and 226 when support structure 234 is mated with base assembly 152. As best seen in FIG. 3, base assembly 152 has a centrally disposed socket-like recess 244 that closely receives inlet element 240 when structure 234 is mated with base assembly 152.

Formed on either side of element 240 are wing-like protuberances 248 (FIG. 13) which are received within spaced-apart, arcuate-shaped cavities formed in base assembly 152 (not shown). Located proximate the upper edge of support structure 234 are arcuately, spaced-apart connector members 252 which mate with arcuately spaced openings 254 provided on cover 156 to enable secure interconnection of support structure 234 with the reservoir assembly.

As shown in FIG. 3, when the support structure 234 is mated with the reservoir assembly, fluid inlet passageway 242 is placed in fluid communication with reservoir 220 via passageways 224 and 226. With this construction, when fluid is forced through fluid passageway 242 of inlet 240 by the stored energy means, the fluid will flow into a vertically extending passageway 256 formed in a thin manifold plate 260 (FIG. 13) which is closely receivable within a similarly shaped cavity 261 formed in the forward face of element 234 (FIG. 12). Next, the fluid will flow into a horizontally extending passageway 262 formed in manifold plate 260 and finally into a chamber 264 formed in a distendable, elastomeric first boot 266 of the flow indicator means of the invention. As shown in FIG. 13A, boot 266 includes a yieldably distendable fluid flow blocking body portion 266a which is circumscribed by a marginal portion 266b. Marginal portion 266b is clamped between manifold plate 260 and a uniquely configured indicator base 268 so that the boot extends through a generally arcuate-shaped opening 268a formed in the indicator base 268. It is to be understood that, when the fluid flowing from reservoir 220 fills passageways 256 and 262 and impinges upon boot 266, flow will be diverted back in the direction of arrows 269 of FIGS. 12 and 13 toward support structure 234 and into a chamber 270 which is formed in the rear surface of the support structure (FIG. 13). Chamber 270 is adapted to closely receive an angularly shaped insert 271 of the character shown in FIG. 12. As shown in FIG. 12, insert 271 includes a horizontally extending fluid passageway 272 having an inlet end 272a and an outlet end 272b. Insert 271 also has a vertically extending fluid passageway 274 having an upper inlet end 274a and a lower outlet end 274b which terminates in a socket-like cavity 276. Cavity 276 is in communication with a tubular quick-connect coupling 280 formed on support structure 234 (FIG. 12). In a manner presently to be described, tubular extension 280 is adapted to mate with a quick disconnect outlet adapter 280a which is, in turn, connected to the fluid delivery line 281 of the apparatus (FIG. 1).

It is to be observed that fluid which is diverted back from boot 266 toward support structure 234, will flow in the direction of the arrow 269 of FIG. 13, through rate control element 230, and then into inlet end 272a of passageway 272 formed in insert 271. After flowing through rate control element 230, the fluid will next flow along passageway 272 toward the outlet end 272b in the direction of arrow 283 (FIG. 13) and then outwardly of the passageway through an outlet port 284 formed in support structure 234. Next, the fluid will flow forwardly in the direction of arrow 286 through an orifice 288 formed in plate 260 where it will impinge on a second elastomeric, distendable boot 286 which also forms a part of the indicator means of the invention. Indicator boot 286, which is of identical construction to boot 266, is clamped within an oval shaped opening 268b formed in indicator base 268. After impinging on boot 286, the fluid will next flow back toward support structure 234 in the direction of arrow 287, through a lower orifice 290 formed in plate 260 and then, via orifice 291 formed in structure 234, into the upper inlet end 274a of passageway 274 which is formed in insert 271. Upon entering passageway 274, the fluid will flow downwardly of the passageway into cavity 276 and then into tubular extension 280 where it can enter the quick disconnect outlet adapter 280a and finally delivery line 281.

It is to be noted that fluid flowing from reservoir 220 into passageway 240 and then on toward boot 266 is under a higher pressure than fluid flowing toward boot 286. This is because the pressure of the fluid flowing toward boot 286 has been reduced as a result of the fluid flowing through rate control element 230. It should also be noted that vent means, shown here as a vent patch 287, is provided in the system to permit air trapped within the flow control assembly to be vented via a port 289 formed in plate 260.

Next to be considered is the important flow indicator means of the invention, which functions to distinguish among three conditions of operation, namely normal fluid flow, fluid flow blockage or occlusion, and reservoir empty. Turning particularly to FIGS. 3, 12, and 13, the flow indicator means here comprises the previously identified indicator base or platform 268, as well as the boot clamping plate 260. Additionally, the indicator means comprises a support or lens plate 300, and a hollow housing 302 within which the platform and the support plate are enclosed (FIG. 3). As seen in FIG. 3, a viewing lens 301 is viewable through an aperture 302a provided in housing 302.

Disposed between platform 268 and plate 300 are first and second indicia-carrying means shown here as a pair of closely adjacent, thin films. These films, identified here as 306 and 308, are in intimate contact and are preferably constructed from a substantially transparent, flexible polymer material such as mylar. It is to be understood that the indicia-carrying means need not be thin films, but rather can be any type of surface presenting member upon which indicia can be provided. The downstream surface of the inferior or first film 306 is printed with three integrated symbols 307 (FIG. 12), which may comprise, by way of example, a blue circle, a green arrow, and a red X, each consisting of diagonal strips of color printed in an alternating pattern (blue, green, red, blue, green, red, and so on (see also FIGS. 25 through 29 of U.S. Ser. No. 08/432,221 which is incorporated herein by reference). The second film 308 serves as a "mask" over film 306 and is printed with a pattern of diagonal alternating clear and opaque strips 308a that occur in approximately a 1:2 ratio. The printed ratio of the "mask" allows only one colored symbol to appear at a time when viewed through viewing lens 301. The inferior and superior films are provided at their opposite ends with apertures 310 which receive retention pins 312 provided on platform 268 (FIG. 12) which permit attachment of the film to platform 268 in a manner such that the non-patterned portions of each film covers boot openings 268a and 268b provided proximate each end of platform 268 with the patterned portions of both the superior and inferior films being maintained in index. With this construction, each thin film is able to move in response to pressure exerted thereon by the elastomeric boots in opposing directions parallel to the film plane with its range of motion limited to one axis in the film plane by edge guides 318 provided on platform 268 (FIG. 12). As the films move, the visible symbol pattern will, of course, change due to the transverse displacement of the patterns imprinted thereon.

As is apparent from a study of FIG. 13, the central portions of both the first and second elastomeric actuator elements or boots 266 and 286 will be deflected outwardly toward plate 300 when the device is filled and primed, but not in a state of delivery or when there is a build up of fluid pressure during delivery that is caused by blockage of the delivery line downstream from boot 286. While boot 266 can be deflected by normal line pressure, boot 286 is deflected only by pressure buildup resulting from the downstream blockage. When both elastomeric boots 266 and 268 are deflected outwardly, both the superior and inferior films are displaced transversely to a second position revealing a second symbol, as for example, an X as viewed through the viewing aperture of the support plate (see also FIGS. 28 and 29 of U.S. Ser. No. 08/432,221 which is incorporated herein by reference).

Figure 24:
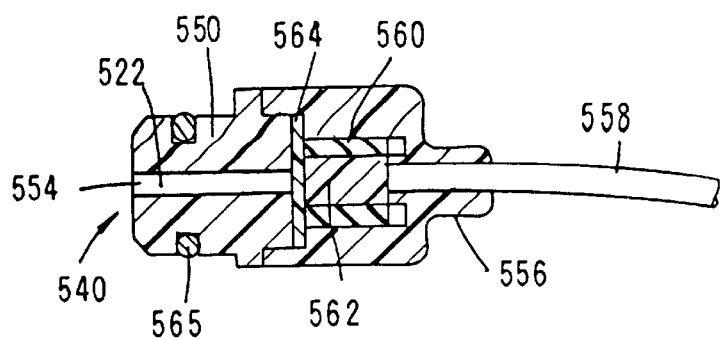
FIG. 24 is a view of the flow control means of FIG. 23 shown in assembled configuration.

A third alignment of symbol patterns as shown in FIGS. 24 and 25 of U.S. Ser. No. 08/432,221 (which is incorporated herein by reference) is visible when the device is in an unfilled state or when the delivery line is open, the reservoir is empty and fluid delivery to the patient has been completed. In this case, there is no fluid pressure in the line on either the upstream or the downstream side of the flow control means and thus both the first and second boots are in a non-deflected position. In this condition, the inferior and superior films are not transversely displaced and thus exhibit a third combination of patterns resulting in a third symbol as, for example, a circle being visible through the viewing aperture of the support plate. Boots 266 and 286 can be precisely tailored to deflect under various pressures thereby permitting great apparatus versatility.

Figure 9:
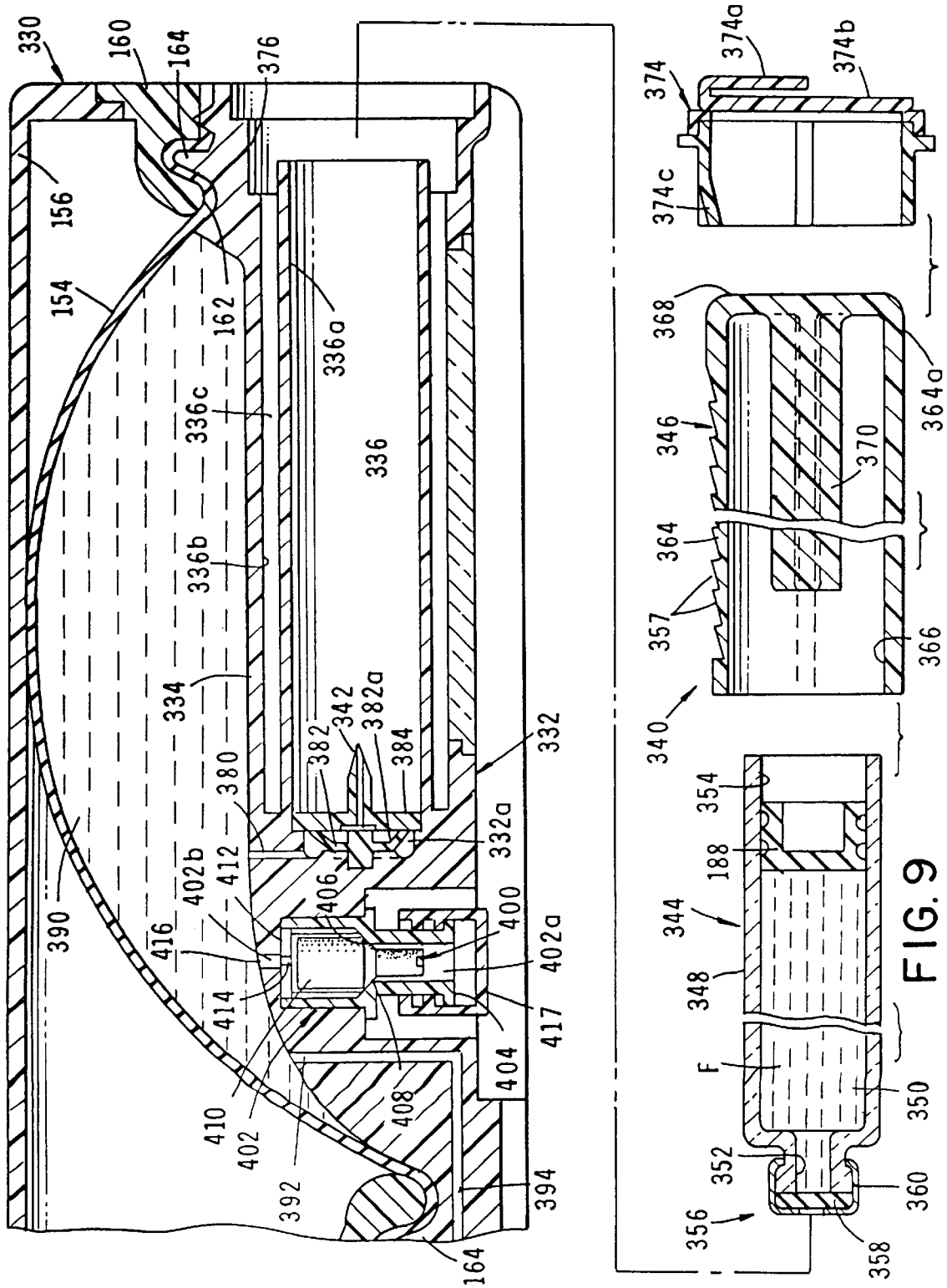
FIG. 9 is a side-elevational, cross-sectional, exploded view showing an alternate form of the apparatus of the invention in which the blunt end cannula of the reservoir assembly has been replaced with a needle like piercing cannula.

Turning next to FIGS. 7 through 9, still another form of the apparatus of the invention is there shown and generally designated by the numeral 330. This embodiment is similar in many respects to the embodiment shown in FIGS. 1 through 8 and like numerals have been used to identify like components. More particularly, only the reservoir and fill subassemblies of the device have been modified, with the flow rate control subassembly and the indicator subassembly of the device remaining unchanged.

With regard to the modified reservoir subassembly which is shown in FIG. 9, this subassembly includes a base assembly 332, a distendable membrane component 154, and a cover 156 for enclosing the membrane. While the base assembly 332 includes a slightly modified ullage substrate 334, the membrane capture housing 160 is virtually identical to that previously described and includes a bottom opening 162 which receives the basically unchanged distendable membrane engaging element or protuberance 164 of base assembly 332. As before, the modified ullage substrate 334 is provided with fill assembly receiving means shown here as a longitudinally extending, generally cylindrically shaped receiving chamber 336 for receiving the fill assembly 340 which is also of a slightly different construction from that shown in FIGS. 1 through 8. As best seen in FIG. 9, the cannula means of the latest form of the invention comprises a sharp, needle-like, hollow cannula 342, rather than a blunt end cannula.

The fill assembly 340 of this latest embodiment of the invention comprises a container subassembly 344 and an adapter subassembly 346. Container subassembly 344 includes a body portion 348, having a fluid chamber 350 for containing an injectable fluid "F". Chamber 350 is provided with first and second open ends 352 and 354. First open end 352 is sealably closed by closure means here provided in the form of a pierceable septum assembly 356 which includes a septum 358. Septum 358 is pierceable by the needle-like sharp cannula mounted within receiving chamber 336. Septum 358 is held securely in position within open end 352 by clamping ring 360. As before, in order to expel fluid from chamber 350, a plunger 188 is telescopically movable within the chamber from a first location where it is proximate second open end 354 to a second position where it is proximate first open end 352.

The adapter subassembly 346 of this form of the invention comprises a hollow housing 364 having a first open end 366 and a second closed end 368. Container subassembly 344 is telescopically receivable within open end of chamber 336, then the adapter subassembly 346 is introduced to open end of chamber 336 when pusher rod engages plunger of vial. Adapter subassembly 346 also includes an elongated pusher rod 370 which functions to move plunger 188 within fluid chamber 350 from a first extended position to the second position proximate septum assembly 356 as the fill assembly is mated with the reservoir assembly.

As best seen in FIG. 9, provided within chamber 336 is an inner cylindrically shaped wall 336a which is concentric with the inner wall 336b of receiving chamber 336, forms an integral part of ullage substrate 334 and is radially spaced from the inner wall 336b of chamber 336 so as to define a longitudinally extending annular space 336c. With this construction, during the mating of the reservoir fill assembly with the reservoir assembly, the outer wall 364a of hollow housing 364 is closely receivable within space 336c as the adapter subassembly is urged inwardly of chamber 336. At the same time that wall 364a moves forwardly of annular space 336c, the container assembly telescopes inwardly of hollow housing 364 and is guided thereby so as to move septum 358 into piercing engagement with sharp end cannula 342.

Prior to the reservoir fill assembly being mated with the reservoir assembly, chamber 336 is maintained in a sterile condition by a sterile tear-off cover assembly 374 which is bonded or otherwise removably affixed to the wall of a counter bore 376 formed in ullage substrate 334. An integral pull tab 374a is provided to permit the cover 374b to be pulled free so as to permit insertion of the reservoir fill assembly into chamber 336. Cover assembly also includes an inwardly extending tab 374c which engages teeth-like protuberances 357 formed on wall 364a of the fill adapter so as to prevent removal thereof after the fill assembly has been mated with the reservoir assembly.

As plunger 188 of the container assembly is moved forwardly of container 344 by pusher rod 370, the fluid contained in the container will flow under pressure into a passageway 380 via hollow cannula 342 and via an umbrella type check valve 382 which is of similar construction and operation to valve 209. Valve 382 is received within a cavity 332a formed in the end wall of receiving chamber 336 and is held in position therewithin by a disc-shaped member 384 which supports cannula 342 in the manner shown in FIG. 9. Valve 382 is constructed from an appropriate elastomer and has a resiliently deformable skirt portion 382a which will deform inwardly within cavity 332a to permit fluid to flow toward the reservoir of the device but will block reverse flow. From passageway 380, the fluid will flow under pressure into reservoir 390 where it will cause the stored energy means or membrane 154 to distend outwardly from ullage substrate 334 n the manner shown in FIG. 9.

After the reservoir has been filled and as membrane 154 moves toward substrate 334 during the fluid dispensing step, fluid within reservoir 390 will be uniformly and controllably forced outwardly through reservoir outlet 392, through a passageway 394 and then into passageway 242 of the fluid inlet to substrate 234 of the flow control means (see for example FIG. 3).

As shown in FIG. 9, the embodiment of this latest form of the invention also includes a uniquely designed auxiliary filling means mounted on ullage substrate 334 which enables filling of reservoir 390 other than by mating the fill assembly 340 with the reservoir assembly. This auxiliary filling means here comprises a generally cylindrically shaped housing 402 having a fluid inlet 402a and a fluid outlet 402b in communication with reservoir 390. Housing 402 terminates at its inlet end in a conventional luer type connector end 404 and includes valve means for controlling fluid flow between inlet 402a and outlet 402b. Valve means 400 here comprises a valve seat 406 which is adapted to sealably engage a tapered shoulder 408 formed on a generally cylindrically shaped valve member 410. Valve member 410 is mounted within housing 402 for reciprocal movement therewithin between a valve closed position shown in FIG. 9 and a valve open position wherein tapered surface 408 is moved away from valve seat 406 a distance sufficient to permit fluid flow toward reservoir 390. An apertured cover 412 closes the upper open end of housing 402 with the aperture 414 which is provided therein in alignment with a reservoir inlet passageway. 416.

In using the auxiliary fill means of the invention, a sanitary closure cap 417, which is temporarily received over luer connector end 404 is first removed. This done, a conventional luer-type connector can be interconnected with end 404 of housing 402 so as to open communication between the interior of housing 402 and a conventional fill line interconnected with the luer connector (not shown). The luer connector and fill line is of standard construction and, in this instance, includes an outwardly extending pintle which engages valve member 410 as the luer connector is mated with housing 402 so as to move valve member 410 into its second open position permitting fluid to flow from the fluid delivery line past valve member 410 and into reservoir 390 via inlet 416. Such a luer connector construction is well understood by those skilled in the art. It is to be observed that the auxiliary fill means can be used as the primary fill means for filling the reservoir or, alternatively, can be used to add an appropriate additive fluid to fluid earlier dispensed into the reservoir 390 by the vial-type fill assembly 340.

Referring next to FIGS. 7 and 8, still another form of fill means of the invention is there shown. This alternate fill means comprises a pistol grip-type fill device 420 which is usable with a reservoir assembly of the character shown in FIG. 8 which is similar in construction to the reservoir assembly shown in FIG. 9. As best seen in FIG. 7, fill device 420 includes a hollow barrel portion 422 and an interconnected hand grip portion 424. Provided at the forward end of barrel portion 422 is a septum assembly 426 which includes a pierceable septum of the same general character as pierceable septum 358 shown in FIG. 9. Provided at the opposite end of barrel 420 from septum assembly 426 is a connector means 428 for interconnecting the interior of barrel portion 422 with a fill line 430 which is, in turn, connected to a pressurized source of medicinal fluid of the character to be used in the filling of reservoir 390.

The fill means of this latest form of the invention is used in connection with the modified reservoir assembly shown in FIG. 9 by holding the reservoir in one hand in the manner shown in FIG. 8. With the pistol grip fill means held in the other hand as shown in FIG. 8, barrel 422 is inserted into chamber 336 and pushed forwardly of the base assembly to cause cannula 342 to pierce septum assembly 426 thereby opening communication between supply line 430 and reservoir 390 of the reservoir subassembly. It is to be understood that the reservoir assembly usable with the pistol grip filling means shown in FIG. 7 can also be of the character shown in FIG. 4 which is provided with a blunt end cannula 185 rather a needle-like cannula 342 as shown in FIG. 8. In this instance, the septum assembly 426 will, of course, embody a split septum rather than a needle-piercing septum so as to accommodate the blunt-end cannula.

Figure 10:
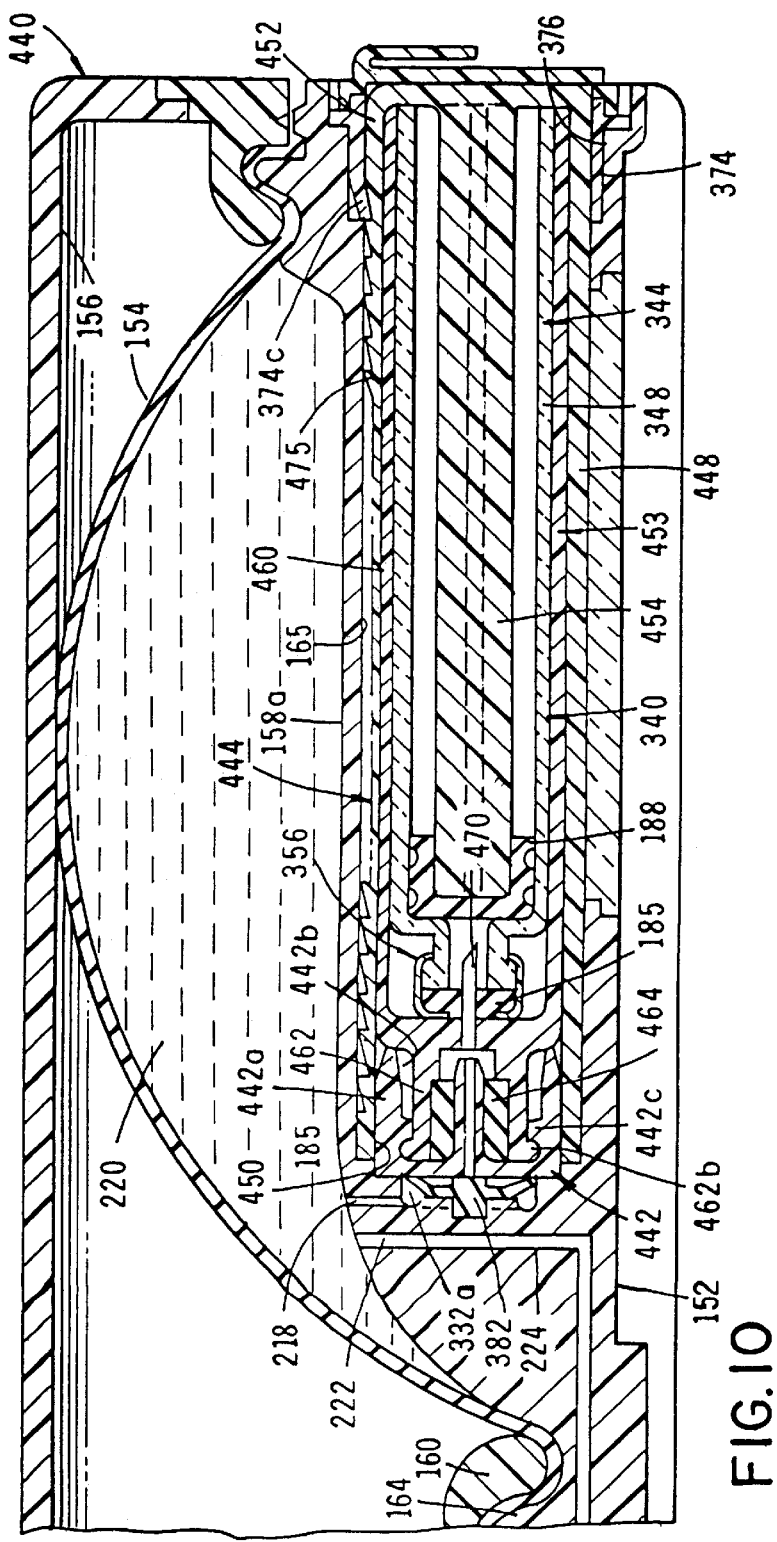
FIG. 10 is a side-elevational, cross-sectional view of an apparatus similar to that depicted in FIG. 3, but showing an alternate form of reservoir fill assembly that uniquely embodies an adapter subassembly that permits a vial assembly having a needle-type pierceable septum to be mated with a reservoir assembly such as shown in FIG. 3 which has a blunt end cannula.
Figure 11:
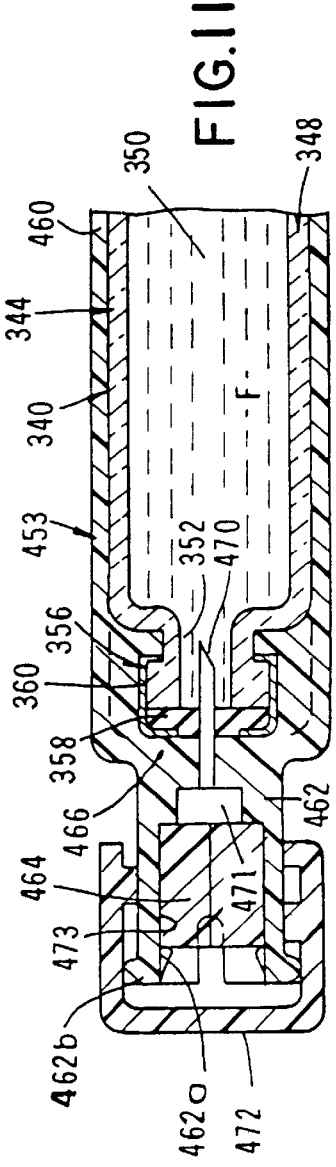
FIG. 11 is an enlarged fragmentary, cross-sectional view of a proportion of the adapter subassembly shown in FIG. 10 with a portion of a vial assembly having a needle piercing cannula mated therewith.

Turning next to FIGS. 10 and 11, still another embodiment of the invention is there shown and generally designated by the numeral 440. This embodiment is also similar in many respects to the embodiment shown in FIGS. 1 through 8 and like numbers have been used to identify like components. More particularly, only the fill assembly 444 and the housing 442, which supports the blunt end cannula 185, have been modified with the remainder of the device remaining unchanged. The main purpose of this latest embodiment of the invention is to provide means for coupling a container assembly having a standard needle piercing septum with a reservoir assembly having a blunt end cannula.

As shown in FIG. 10, modified housing 442 of the reservoir assembly of this latest form of the invention supports the blunt end cannula 185 in the manner previously described. However, the inner wall 442b of the skirt portion 442a thereof is provided with a circumferentially extending bead or protuberance 442c which, in a manner presently to be described, lockably engages a portion of the modified fill assembly 444.

The modified fill assembly 444 of the form of the invention shown in FIGS. 10 and 11 comprises a hollow housing 448 having a first open end 450 and a closed second end 452. The container subassembly, which is of identical construction to the container subassembly 340 shown in FIG. 9, is telescopically receivable within the open end 453a of a second housing 453 which is, in turn, receivable within housing 448 in the manner shown in FIG. 10. Second housing 453 is of a novel generally cylindrically shaped construction of a character presently to be described. As shown in FIG. 10, assembly 444 includes an elongated pusher rod 454 which, as the fill assembly is mated with the reservoir assembly, functions to move plunger 188 of the container subassembly telescopically of fluid chamber 350 from a first extended position to the second position proximate septum assembly 356.

As best seen by referring to FIG. 11, second housing 453 includes a hollow, central body portion 460 and a forward end portion 462 having an open end 462a and a circumferentially extending bead or protuberance 462b surrounding open end 462a. Sealably closing open end 462 is a split septum 464 which is of a conventional construction adapted to sealably receive a blunt end cannula such as cannula 185 which is carried by modified housing 442.

Extending through and supported by a wall 466 which divides body portion 460 and forward portion 462 of second housing 453 is a sharp needle-like hollow cannula 470 which is adapted to sealably pierce septum 358 of container assembly 340.

In using the apparatus of this latest embodiment of the invention, container assembly 340 is first inserted into open end 453a of second housing 453 and is urged forwardly to the position shown in FIG. 11 wherein needle-like cannula 470 pierces septum 358. This step opens communication between fluid chamber 350 of the container assembly and a subchamber 471 formed in the forward portion 462 of second housing 453 and in communication with chamber 473 which sealably receives split septum 464. After removing a protective cap 472 which closes open end 462a of forward portion 462 the assembly made up of second housing 453 and fluid container assembly 340 is mated with hollow housing 448. The assemblage is then urged forwardly of chamber 165 which causes pusher rod 454 to move plunger 188 of the container assembly forwardly of chamber 350. As the assemblage seats the split septum 464 will be sealably pierced by blunt end cannula 185. This step opens fluid communication between chamber 350 of the container subassembly and chamber 332a which houses check valve 382. As before, as the fluid contained within chamber 350 of the container subassembly is urged outwardly of the container by forward movement of plunger 188, the fluid contained within the container assembly will flow through hollow needle 470, through hollow blunt end cannula 185, past umbrella check valve 382 and into reservoir 220 via inlet portion 218. As shown in FIG. 10, when the fill assembly seats within receiving chamber 165, protuberance 462b formed on second housing 453 will move past protuberance 442c formed in skirt 442a of the cannula support housing thereby locking second housing 453 against removal from the reservoir assembly. Similarly, tab 374c formed on closure cap assembly 374 will lockably engage the saw tooth shaped protuberance 475 formed on housing 448 so as to prevent removal of housing 448 from the reservoir assembly.

It is apparent that with this latest embodiment of the invention, a container subassembly of the character shown in FIG. 9 which has a standard septum 358 can be readily mated with an apparatus of the character shown in FIG. 10 which embodies a blunt end cannula 185, without having to modify either the container subassembly or the reservoir assembly.

Figure 14:
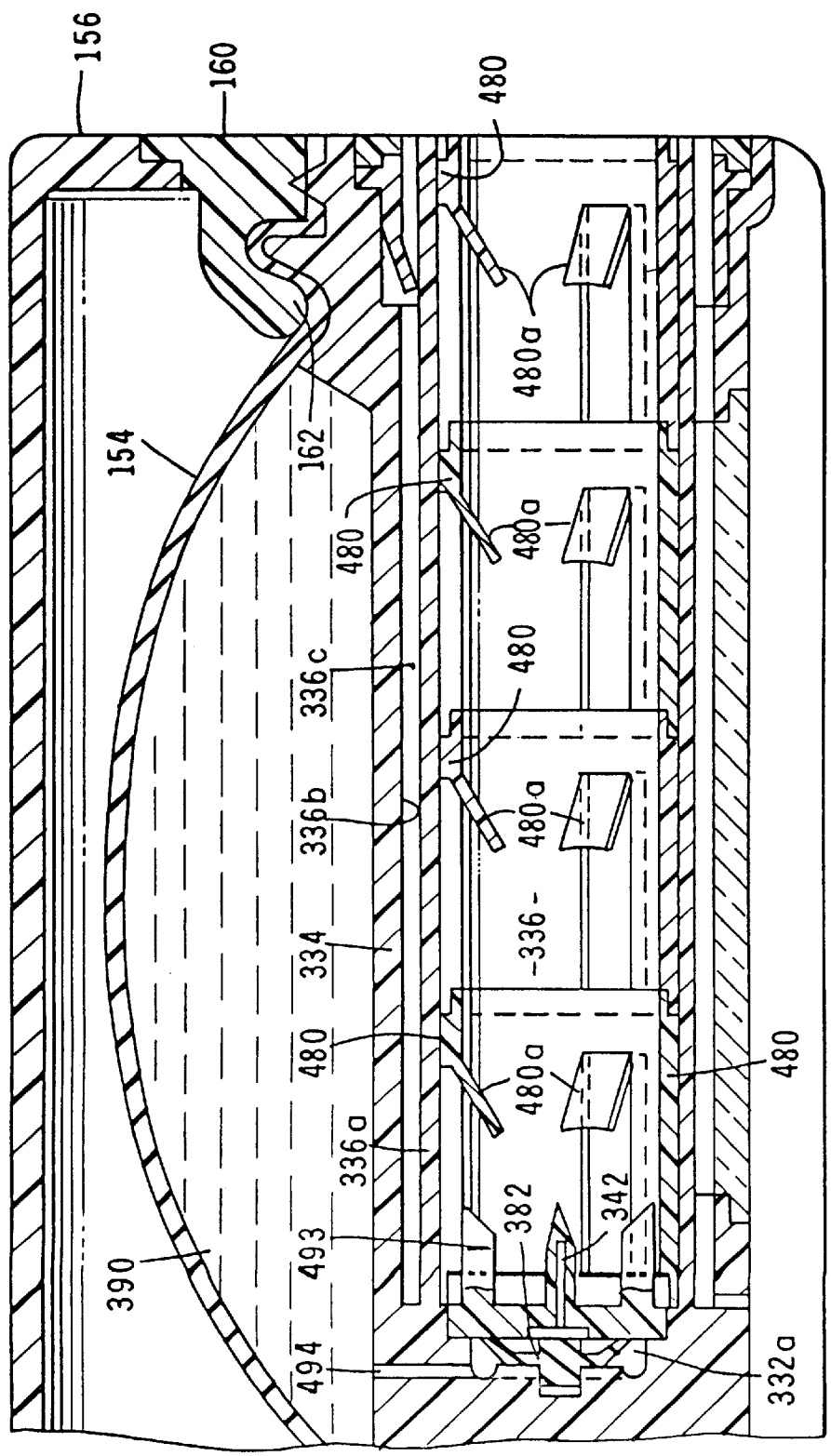
FIG. 14 is a fragmentary, side-elevational, cross-sectional view of still another form of reservoir assembly of an alternate embodiment of the invention.
Figure 15:
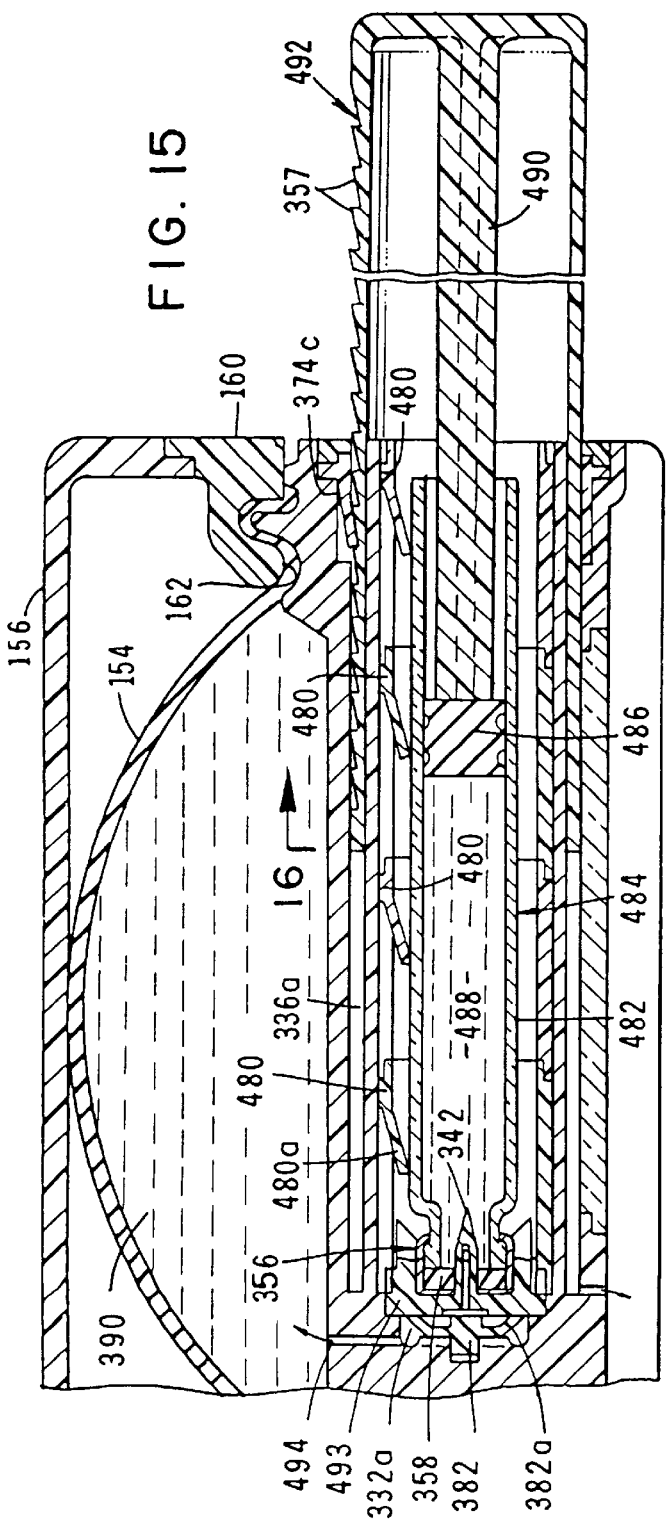
FIG. 15 is a fragmentary, side-elevational, cross-sectional view similar to FIG. 10, but showing the fill means of this alternate form of the invention being mated with the reservoir assembly.
Figure 16:
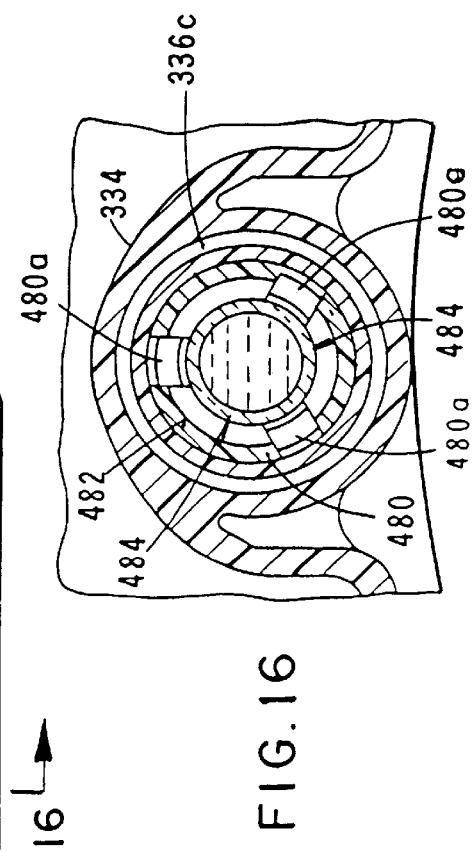
FIG. 16 is an enlarged, cross-sectional view taken along lines 16—16 of FIG. 15.

Turning to FIGS. 14, 15, and 16, yet another embodiment of the invention is there illustrated. This embodiment is generally similar to the embodiment shown in FIG. 9 save that the reservoir assembly does not include the secondary fill means and save for the fact that the cannula means is of a slightly different construction. Also different from the embodiment of the invention shown in FIG. 9 is the fill means of the invention which is here designed to accommodate a fluid container subassembly which has a diameter substantially less than the internal diameter of wall 336a of the base assembly. Because of the similarity of construction, like numerals are used to identify like components.

As best seen in FIG. 15, to accommodate a smaller diameter container assembly of the character there shown, a plurality of ring-like guide members 480 are positioned at longitudinally spaced apart locations along inner wall 336a. Each of these ring-shaped guide members 480 includes a plurality of circumferentially spaced, resiliently deformable tabs 480a which extend inwardly relative from wall 336a and function to guidably engage the outer wall of body portion 482 of the fluid container assembly 484 of this latest form of the invention (FIG. 15). Container assembly 484 includes a septum assembly 356 of the same general construction as shown in FIG. 9, the pierceable septum 358 of which is adapted to be pierced by the sharp end, needle-like cannula 342 which is supported by a slightly differently configured cannula support 493. As before, a plunger 486 of the container assembly is moved longitudinally of fluid chamber 488 by a pusher rod 490 which forms a part of the hollow housing 492 of the adapter portion of the fill means. As before, as housing 492 of the fill means is inserted into annular space 336c in the manner shown in FIG. 15, pusher rod 490 will move plunger 486 forwardly of the fluid container assembly causing fluid flow through cannula 342, past check valve 382, and into fluid reservoir 390 via an inlet 494. As adapter sleeve 492 is mated with the reservoir assembly, the fluid container assembly will remain perfectly centered with respect to pusher rod 490 due to the guiding action of tabs 480a of guide rings 480.

Figure 17:
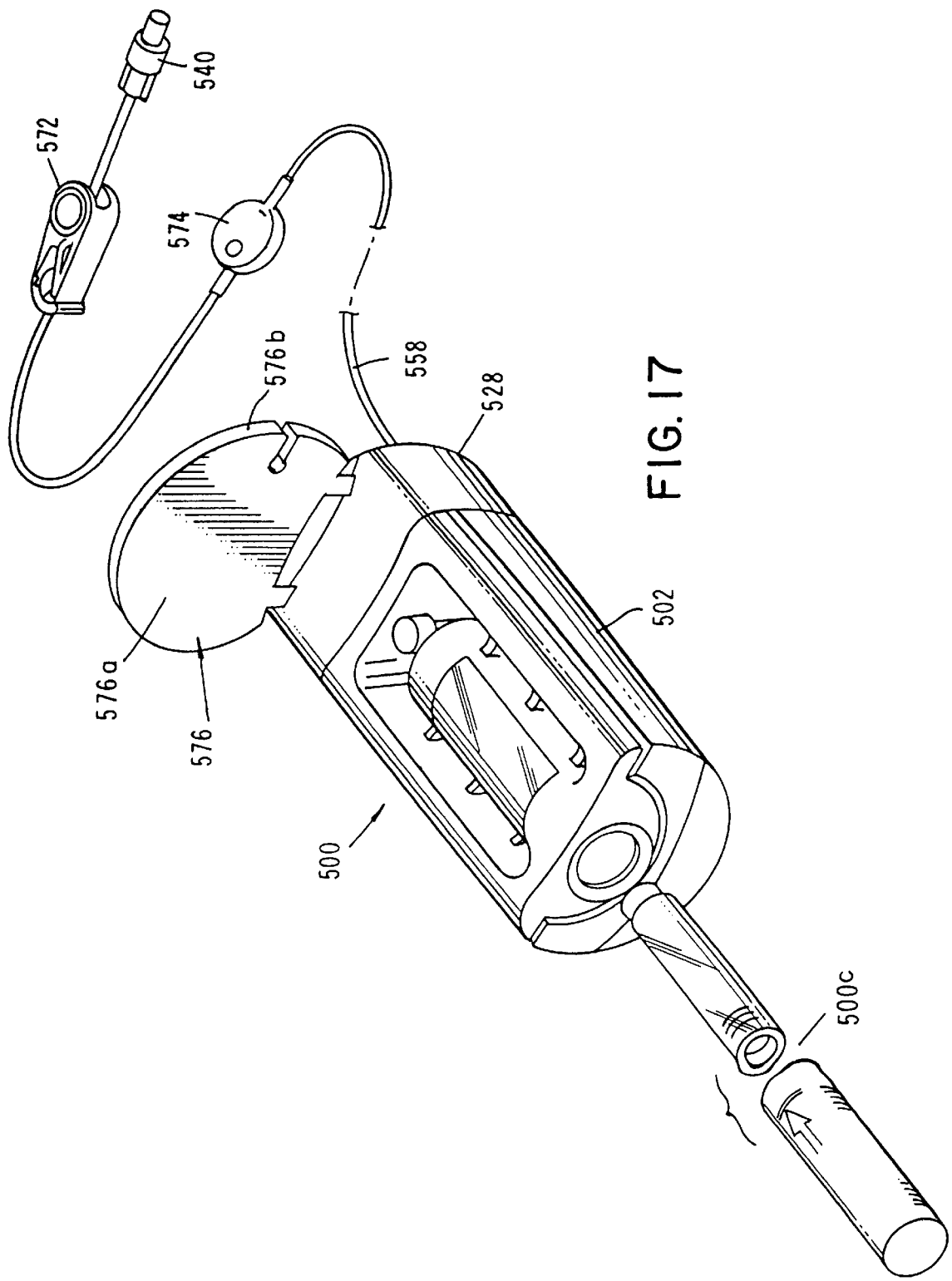
FIG. 17 is a generally perspective bottom view of an alternate form of the fluid delivery apparatus of the invention.
Figure 18:
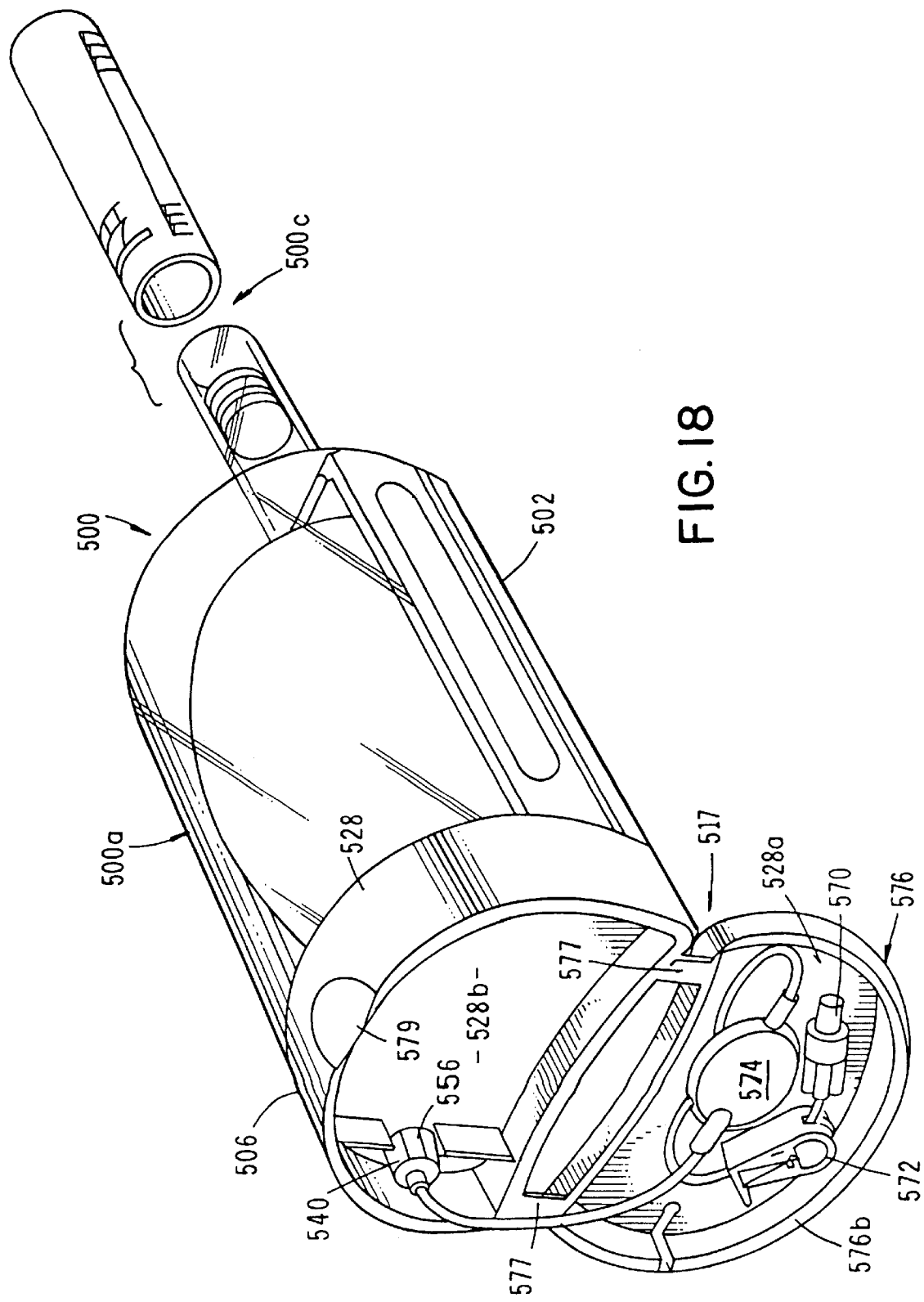
FIG. 18 is a generally perspective, top view of the apparatus shown in FIG. 17.
Figure 19:
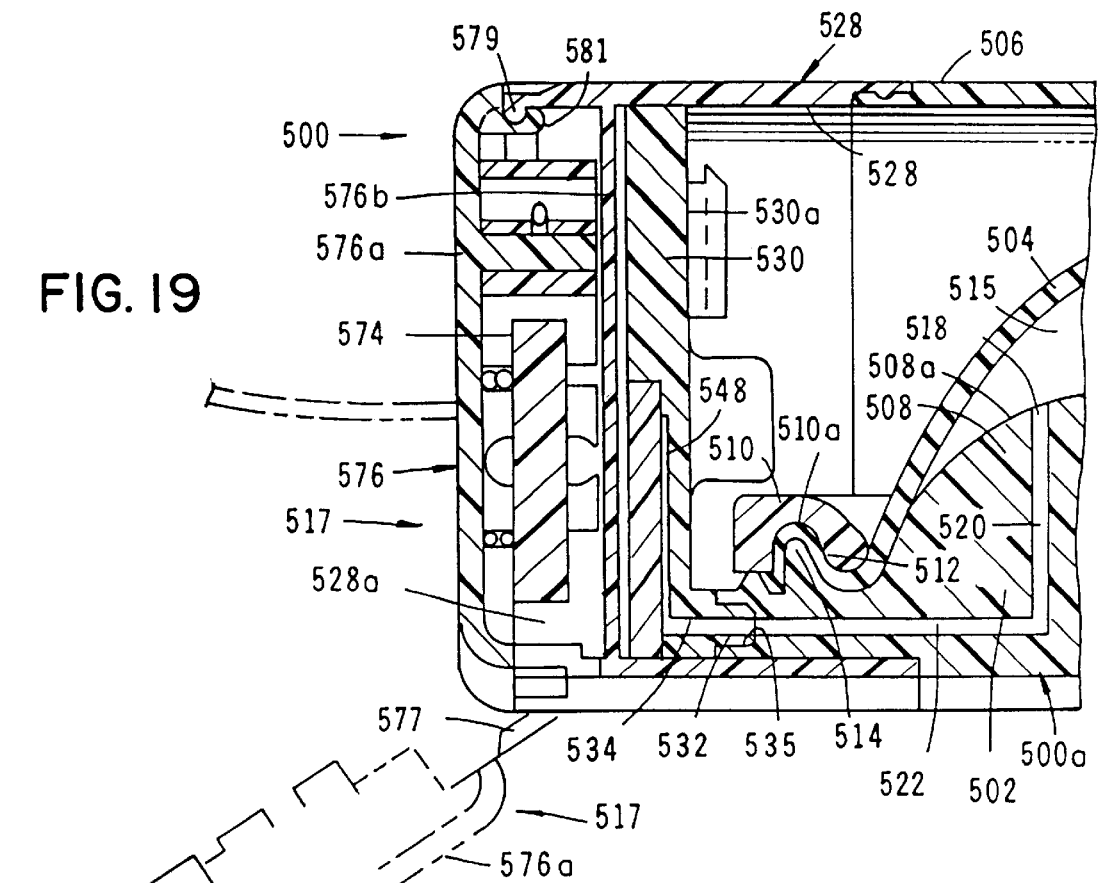
FIG. 19 is a fragmentary, cross-sectional view of the forward portion of the form of the fluid dispensing apparatus shown in FIG. 18.

Turning next to FIGS. 17 through 26, yet another form of the apparatus of the invention is there shown and generally identified by a numeral 500. This form of the apparatus is similar to that illustrated in FIGS. 1 through 5 and like numbers are used to identify like components. However, in this latest embodiment only three major cooperating subassemblies are provided, namely, a reservoir subassembly 500a, a flow rate control subassembly 500b (FIG. 24), and a fill assembly 500c (FIG. 18). An important feature of this latest embodiment is the provision of a highly novel closure means for closing the forward end of the device. This closure means, which is best seen in FIGS. 18 and 19 and is generally designated therein by the numeral 517. This important closure means will be further described in the paragraphs which follow.

As indicated in FIG. 19, the reservoir subassembly 500a of this latest embodiment is quite similar to that shown in FIG. 3 and includes a base assembly 502, a stored energy source, shown here as a distendable membrane component 504, and a cover 506 for enclosing the stored energy source in the manner previously discussed The base assembly, only a portion of which is shown in FIG. 19, is of the same basic design as base assembly 152 and includes an ullage substrate 508 as well as a membrane capture housing 510 which is of identical construction to previously described capture housing 160. Housing 510 includes a bottom opening 512 which receives the distendable membrane engaging element or protuberance 514 (see also FIG. 5) of base assembly 502.

As before, ullage substrate 508 is provided with fill assembly receiving means which takes the form of a longitudinally extending, generally cylindrically shaped receiving chamber which is similar in construction to previously described chamber 165 (FIG. 3), and which function to receive a fill assembly 500c which assembly is identical to fill assembly 150d. Valve and cannula means of identical construction and operation to that previously described are disposed within the fill assembly receiving chamber and cooperate with the fill assembly to fill reservoir 515.

As in the earlier discussed embodiments, the stored energy means can take the form of a single prestressed or unstressed isotropic, elastomeric distendable membrane, or it can comprise a laminate assemblage made up of a plurality of initially generally planar distendable elements or films. As the distendable membrane 154 is distended by the fluid pressure exerted by the fluid flowing into reservoir 515, internal stresses are formed therein which continuously urge the assemblage toward engagement with protuberance 508a (FIG. 19) as it tends to return toward its original configuration. As the membrane moves toward protuberance 508a, fluid within reservoir 515 will be uniformly and controllably forced outwardly through reservoir outlet 518, through passageway 520 and finally through a longitudinally extending passageway 522 which is formed in ullage substrate 508 (FIG. 19).

As previously discussed, the upstanding tongue of base 502 extends completely about the perimeter of the base and is closely receivable within a groove 510a provided in capture housing 510. When the ullage substrate and the membrane capture housing are assembled in the manner shown in FIGS. 19, 3 and 28, the periphery of distendable membrane 504 will be securely clamped within groove 510a by tongue 514. After the parts are thus assembled, cover 506 is mated with the capture housing 510 in the same manner as is shown in FIGS. 3 and 5 and then is suitably bonded in place.

Turning now to a consideration of the important cover means of this latest form of the invention, this means here comprises a housing assembly 528 which is interconnected with the reservoir subassembly 500a and functions to close the forward or delivery end of the device (see FIGS. 18 and 19). As best seen in FIG. 19, housing assembly 528 includes a first or forward compartment 528a and a second, or rearward compartment 528b. Rearward compartment 528b houses a support structure 530, which is generally similar in construction to support structure 234 (FIG. 3). Like support structure 234, support structure 530 includes an outwardly extending, generally cylindrically shaped, fluid inlet element 532 within which is provided a fluid passageway 534. When support structure 530 is mated with base assembly 502, passageway 534 will communicate with reservoir 515 via passageways 520 and 522. As before, base assembly 502 has a centrally disposed, socket-like recess 535 that closely receives inlet element 532 when structure 530 is mated with base assembly 502 in the manner shown in the drawings.

Figure 21:
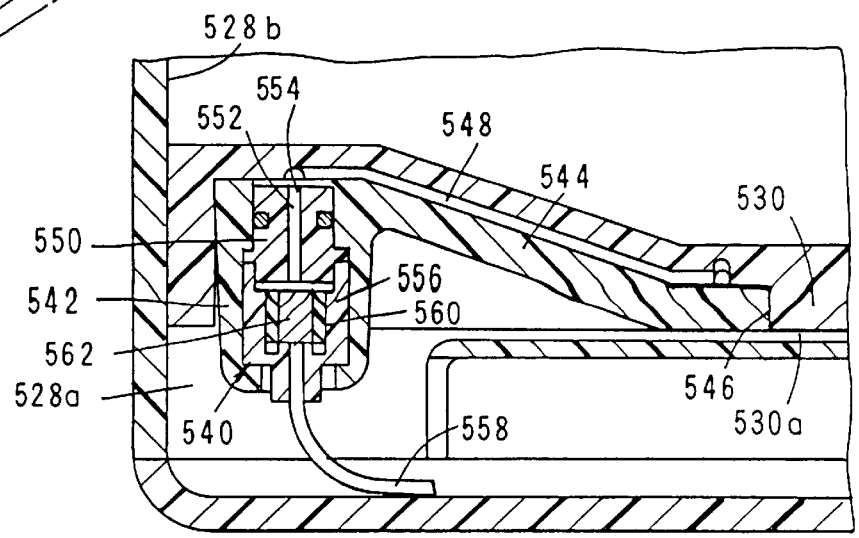
FIG. 21 is a cross-sectional view taken along lines 21—21 of FIG. 20.
Figure 22:
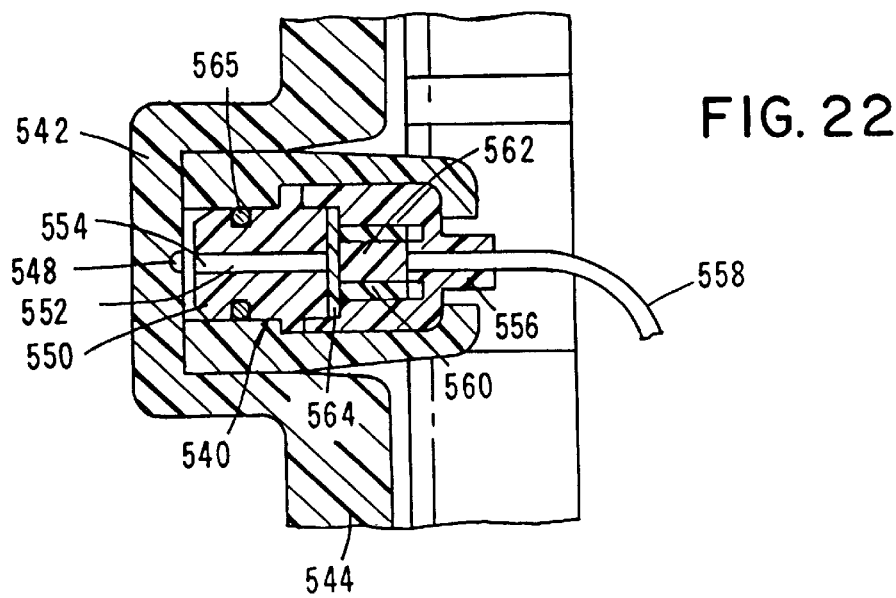
FIG. 22 is a cross-sectional view taken along lines 22—22 of FIG. 20.
Figure 23:
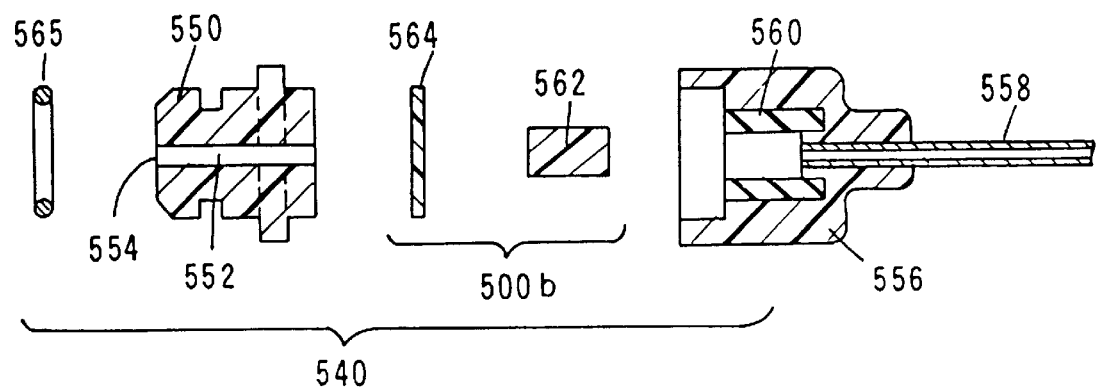
FIG. 23 is an enlarged, exploded, cross-sectional view of the fluid flow control means of this latest form of the invention.

The flow control means of this latest form of the invention for controlling the rate of fluid flow of fluid from the device here comprises a novel flow control assembly 540 of the character shown in FIGS. 23 and 24. As best seen in FIGS. 21 and 22, a rate control assembly 540 is mounted within a socket like portion 542 formed in an insert 544 which is received within a cavity 546 formed in the forward wall 530a of support structure 530 (see FIG. 26). Insert 544, in cooperation with a fluid passageway 548 formed in support structure 530, functions to provide a fluid flow path between reservoir 515 and the flow control assembly 540. More particularly, assembly 540 here comprises a quick disconnect housing 550 which has a central fluid passageway 552 having an inlet 554 which communicates with passageway 548 in the manner shown in FIGS. 21 and 22.

Interconnected with quick disconnect housing 550 is a delivery line housing 556 to which a delivery line 558 is sealably connected. Disposed within housing 556 is an elastomeric compression ring 560 which sealably receives the flow rate control means of this form of the invention, which means is here provided as a generally cylindrically shaped rate control frit 562. Also forming a part of the flow control means of this latest embodiment is filter means, here shown as a filter element 564 which is disposed between frit 562 and quick disconnect housing 550 (FIG. 24). Frit 562 and filter element 564 are preferably constructed from the same type of materials as previously identified herein in connection with the discussion of elements 237 and 239.

When insert 544 is in position within cavity 546 in the manner shown in FIG. 22, quick connect socket portion 542 extends into forward chamber 528a of the closure means. With this construction, the flow control means can be placed in fluid communication with the fluid reservoir of the device by inserting quick disconnect housing 550 into socket portion 542 and then turning it in conventional fashion to securely lock it in position. To prevent leakage of fluid between housing 550 and socket portion 542 an elastomeric O-ring 565 is provided in housing 550 (FIGS. 23 and 24).

Connected to the flow control means is the fluid delivery means of the invention. This latter means, which is uniquely removably stowed within first or forward compartment 528a of the closure means, here comprises a delivery line luer assembly 570 and a line clamp 572 both of which are of conventional construction. Previously identified delivery line 558 is interconnected with luer assembly 570 in the manner shown in FIG. 18. Disposed between the flow control means and luer assembly 570 is a vent means shown here as a conventional gas vent assembly 574 for venting gases trapped within the system to atmosphere.

Forward compartment 528a is formed within an access door 576 which is connected to that portion of the rearward portion of housing 528 which defines rearward compartment 528b, by hinge means here shown as a pair of living hinge elements 577. With this arrangement, door 576 can be pivoted relative to the reservoir assembly from the closed position shown in FIG. 19 to the open position shown in FIG. 18. Door 576, which forms a part of closure means 517, includes a front face 576a which, in cooperation with an interconnected circumscribing wall 576b, forms forward compartment 528a (FIGS. 18 and 20). Latching means, shown here as comprising an arcuate protuberance 579 formed on housing 528, and an arcuate locking tab 581 formed on door 576, cooperate to latchably maintain the door in a normally closed condition (FIG. 19). With this novel arrangement, the delivery means of the invention can remain securely stowed within compartment 528a until time of use.

Figure 27:
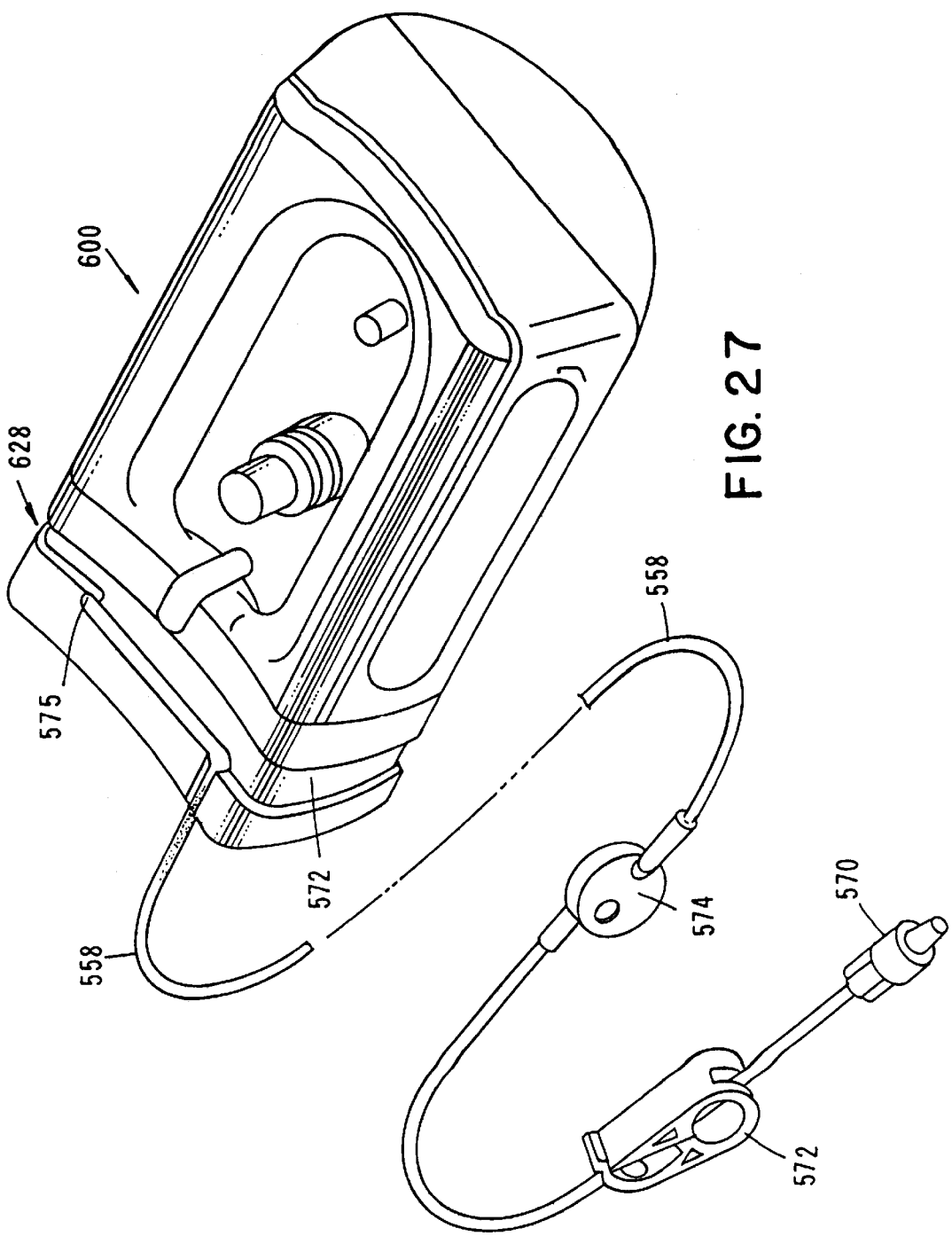
FIG. 27 is a generally perspective, bottom view of another form of the apparatus of the invention.

Turning next to FIGS. 27 through 31, still another form of the apparatus of the invention is there shown and generally identified by a numeral 600. This form of the apparatus is somewhat similar to that illustrated in FIGS. 17 through 25 and like numbers are used to identify like components. In this latest embodiment three major cooperating subassemblies are provided, namely, a reservoir subassembly 600a, a flow rate control means 600b (FIG. 24) and a fluid delivery means 600c which is of the same basic character as is shown in FIGS. 17 and 18. An important feature of this latest embodiment is the provision of a closure means of a slightly different construction for closing the forward end of the device and for stowing the delivery means in cavities provided in the face of the closure means. This closure means, which is best seen in FIG. 27 will be further described in the paragraphs which follow.

Figure 29:
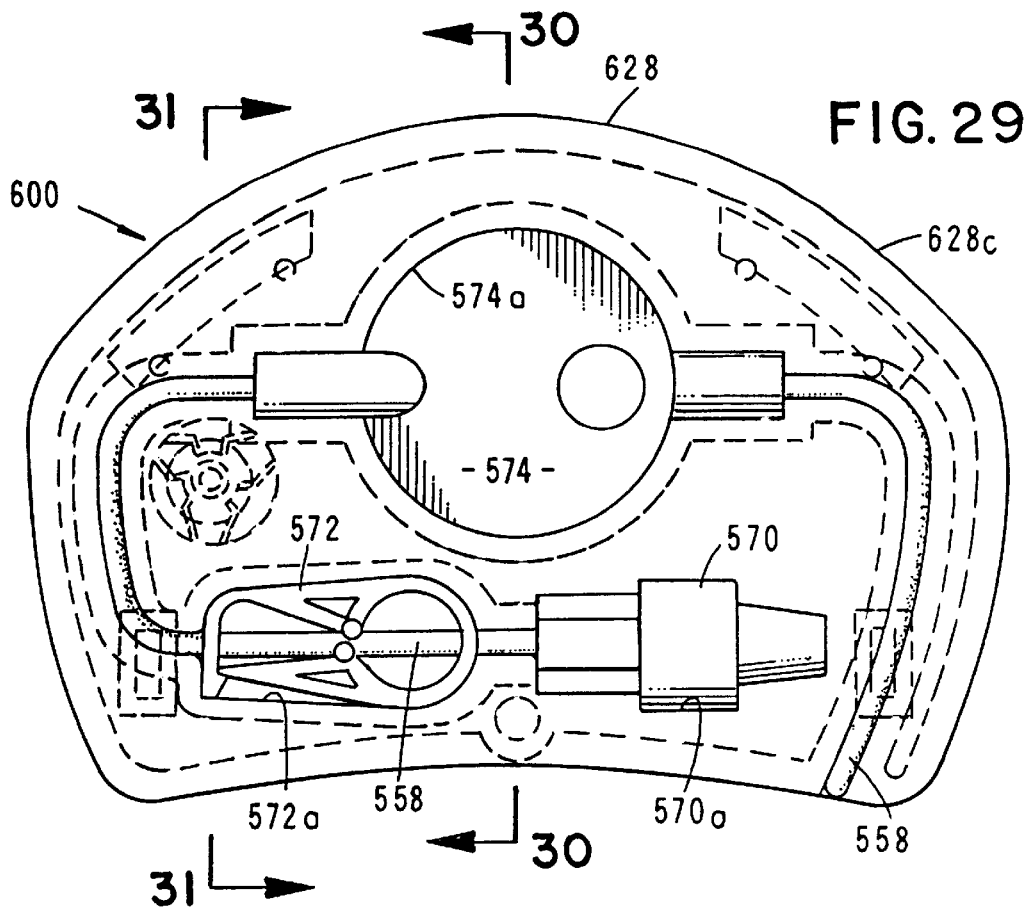
FIG. 29 is a front view of the fluid dispensing apparatus shown in FIG. 28.

As indicated in FIG. 29, the reservoir subassembly 600a of this latest embodiment is virtually identical to reservoir subassembly 500a and, therefore, will not here be described in further detail. Suffice to say that the reservoir subassembly includes a stored energy source, shown as a distendable membrane component 504, and a cover 506 for enclosing the stored energy source in the manner previously discussed. The base assembly, only a portion of which is shown in FIG.

29, is of the same basic design as base assembly 522 and includes an ullage substrate 608 as well as a membrane capture housing 510 which is of identical construction to previously described capture housing 160. Since in this embodiment the reservoir is filled by an external fill line, or the like, no container type fill means is provided and, accordingly, the ullage substrate has no fill assembly receiving chamber. Reference should be made to FIG. 3B of Ser. No. 08/432,221 which is incorporated by reference, wherein the details of construction of the fill means of this latest form of the invention is shown.

Figure 28:
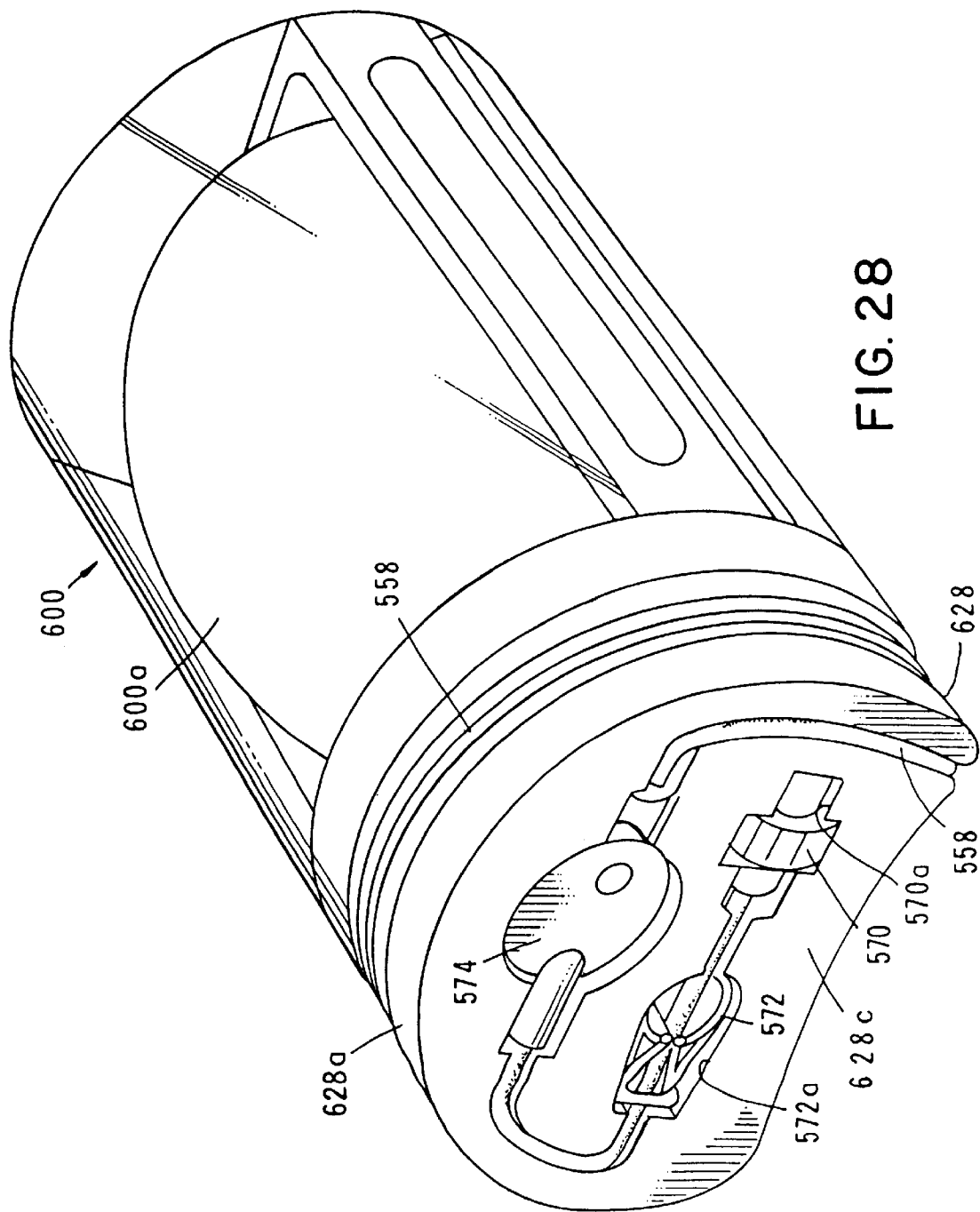
FIG. 28 is a generally perspective top view of the apparatus shown in FIG. 27.
Figure 30:
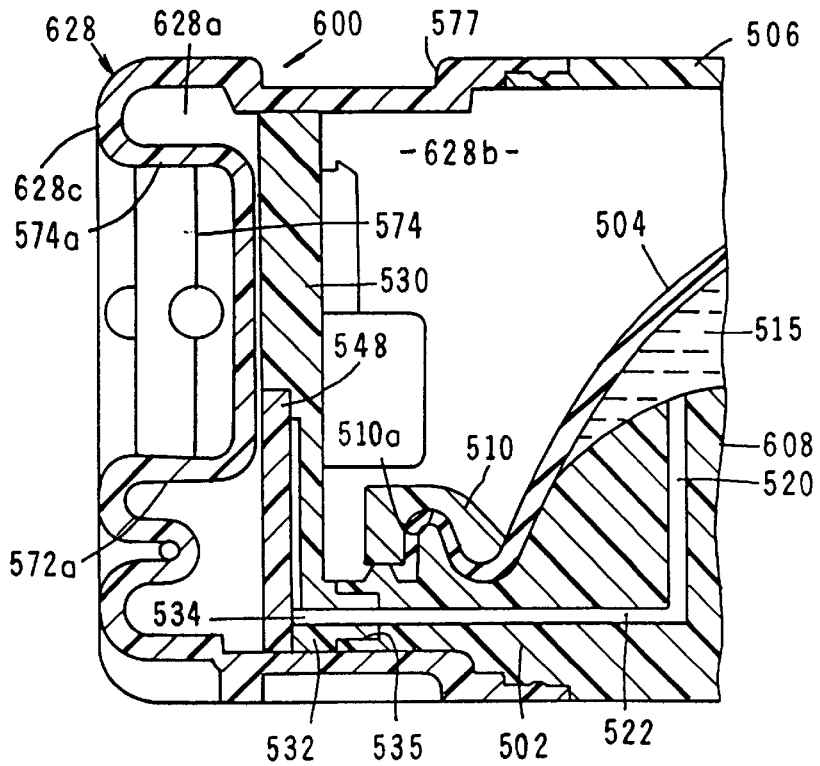
FIG. 30 is a cross-sectional view taken along lines 30—30 of FIG. 29.

With regard to the cover means of the form of the invention shown in FIGS. 27 and 28, this means here comprises a housing assembly 628 which is interconnected with the reservoir subassembly 600a and functions to close the forward or delivery end of the device (see FIGS. 29 and 30). As best seen in FIG. 29, housing assembly 628 includes a first or forward compartment 628a and a second, or rearward compartment 628b. Rearward compartment 628b houses a support structure 530, which is generally similar in construction to support structure 234 (FIG. 3). Like support structure 234, support structure 530 includes an outwardly extending, generally cylindrically shaped, fluid inlet element 132 within which is provided a fluid passageway 534. When support structure 530 is mated with base assembly 502, passageway 534 will communicate with reservoir 515 via passageways 520 and 522. As before, base assembly 502 has a centrally disposed, socket-like recess 535 that closely receives inlet element 532 when structure 530 is mated with base assembly 502 in the manner shown in the drawings.

Figure 31:
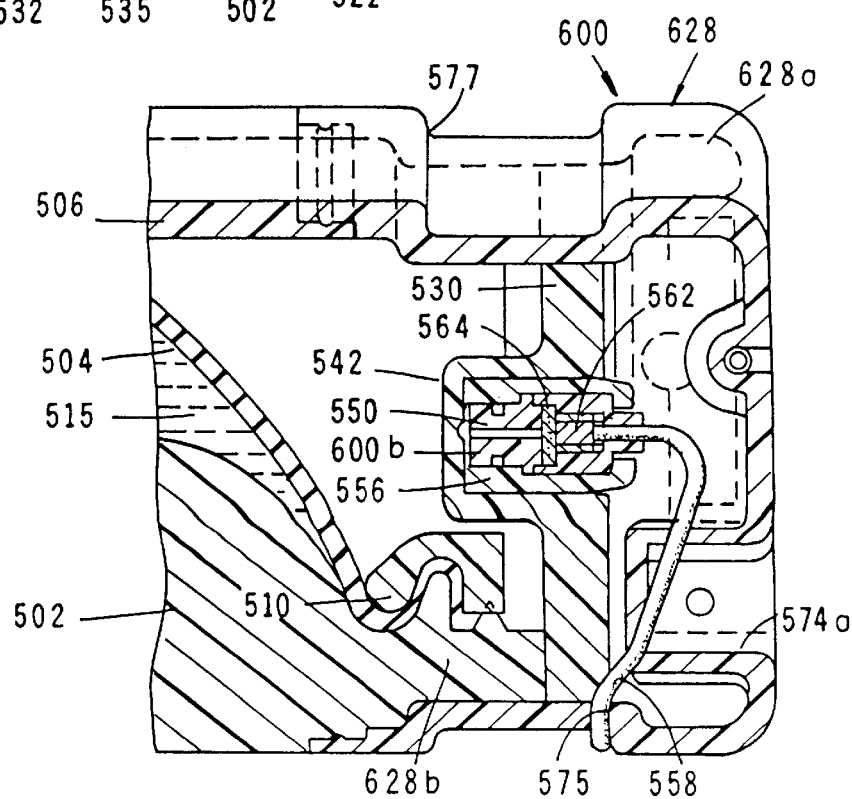
FIG. 31 is a fragmentary, cross-sectional view taken along lines 31—31 of FIG. 29 showing the forward portion of the fluid delivery apparatus.

The flow control means of this latest form of the invention for controlling the rate of flow of fluid from the fluid delivery means of the device is substantially identical to that previously described and comprises a rate control frit 562 and a filter element 564 (FIG. 31). These elements function in the manner described in connection with FIGS. 17 through 25 and are assembled together in the manner shown in FIGS. 23 and 24.

Interconnected to a quick disconnect housing 550 of the character previously described is a delivery line housing 556 to which a delivery line 558 is sealably connected (FIG. 30). As before, when the various components of the flow control assembly 540 are interconnected in the manner shown in FIG. 23 and when the assembly is in position within socket portion 542, the flow control means is in fluid communication with the outlet passageway 520 of the fluid reservoir 515 of the device and is disposed intermediate the outlet of fluid reservoir 515 and delivery line 558 of the delivery means (see FIGS. 29, 30 and 31).

In addition to delivery line 558, the fluid delivery means of this latest form of the invention also comprises a delivery line luer assembly 570 and a line clamp 572 both of which are of the character previously described. Disposed between the flow control means and luer assembly 570 is a vent means shown here as a conventional gas vent and filter assembly 574, which is also of the character previously described.

Figure 32:
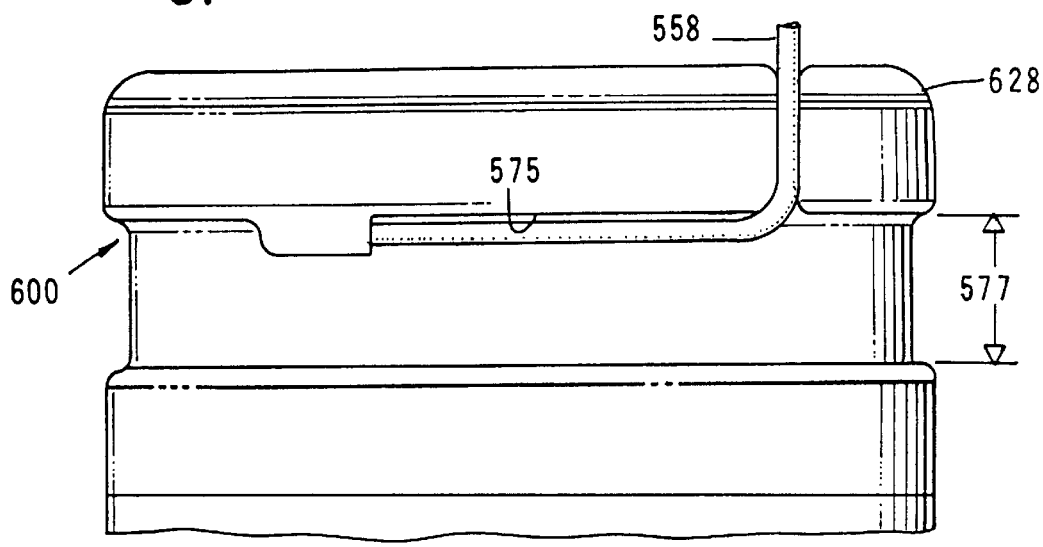
FIG. 32 is a fragmentary top view of the forward portion of this latest form of the invention showing the circumferentially extending channel which is provided for storage of the delivery line of the apparatus.

As best seen in FIGS. 28, 30, and 31, the front face 628c of forward compartment 628a is formed with a plurality of cavity-like recesses which receive portions of the delivery means. More particularly, face 628c has formed therein a cavity 570a which closely receives luer assembly 570, a cavity 572a which closely receives clamp 572 and a cavity 574a which closely receives gas vent assembly 574. Turning to FIG. 31, it is to be noted that delivery line 558 extends downwardly of forward compartment 628a and passes through an opening 575. The line can then be uniquely wound around housing 628 so that it safely resides within a circumferentially extending channel 577 provided in the housing (FIGS. 28, 31, and 32). With this novel arrangement, until the device is to be used, the luer assembly 570, the roller clamp 572, and the vent assembly 574 can be conveniently stowed with the cavities formed in face 628c with the delivery line neatly wrapped around the unit and securely stowed within channel 577. At time of use, the components can be quickly and easily removed from their respective storage cavities and the delivery line expeditiously unwound from the unit. Upon releasing the line clamp 572, and removal of luer aseptic cap 570b (FIG. 26) the stored energy means will then cause fluid to flow through the delivery line at a precisely controlled rate.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

What is claim is:

1. A device for use in infusing medicinal fluid into a patient at a controlled rate comprising:

(a) a reservoir assembly including a base;

(b) stored energy means for forming, in conjunction with said base a fluid reservoir having an inlet and an outlet in said stored energy means comprising at least one distendable member superimposed over said base, said member being distendable as a result of pressure imparted by the fluids to be infused, to establish internal stresses, said stresses tending to move said member toward a less distended configuration;

(c) fluid delivery means in communication with said outlet of said fluid reservoir for delivering fluid from the device;

(d) flow control means disposed intermediate said outlet of said fluid reservoir and said fluid delivery means for controlling the rate of flow of fluid flowing from said fluid delivery means; and (e) closure means connected to said reservoir assembly for supporting therewithin said fluid delivery means.

2. The device as defined in claim 1 in which said closure means comprises a door pivotally movable relative to said reservoir assembly.

3. The device as defined in claim 1 in which said closure means comprises a closure housing having a front face provided with a plurality of component storage cavities.

4. The device as defined in claim 1 in which said flow control means comprises rate control means for controlling the rate of flow of fluid from said fluid delivery means and filter means for filtering fluid flowing from said reservoir toward said rate control means.

* * * * *